US010231632B2

(12) United States Patent
Finlinson

(10) Patent No.: US 10,231,632 B2
(45) Date of Patent: Mar. 19, 2019

(54) APPARATUS AND METHOD FOR TRACKING AND CANCELLING DC OFFSET TO ACQUIRE SMALL AC SIGNAL USING DUAL FEEDBACK LOOPS

(71) Applicant: INTEL CORPORATION, Santa Clara, CA (US)

(72) Inventor: Craig P. Finlinson, Chippenham (GB)

(73) Assignee: Intel Corporation, Santa Clara, CA (US)

( * ) Notice: Subject to any disclaimer, the term of this patent is extended or adjusted under 35 U.S.C. 154(b) by 136 days.

(21) Appl. No.: 15/050,306

(22) Filed: Feb. 22, 2016

(65) Prior Publication Data

US 2017/0238826 A1    Aug. 24, 2017

(51) Int. Cl.
| A61B 5/02 | (2006.01) |
| A61B 5/024 | (2006.01) |
| G05F 1/56 | (2006.01) |
| H03K 5/003 | (2006.01) |

(Continued)

(52) U.S. Cl.
CPC .......... *A61B 5/02427* (2013.01); *A61B 5/725* (2013.01); *G05F 1/561* (2013.01); *H03K 5/003* (2013.01); *H05B 33/0809* (2013.01); *H05B 33/0815* (2013.01); *Y02B 20/347* (2013.01)

(58) Field of Classification Search
CPC  A61B 5/02427; A61B 5/725; H05B 33/0809; H05B 33/0815
See application file for complete search history.

(56) References Cited

U.S. PATENT DOCUMENTS

| 7,176,652 B2 * | 2/2007 | Wakabayashi | .......... H02P 29/50 |
| | | | 318/400.02 |
| 2002/0101270 A1 * | 8/2002 | Nishizono | ............... H03F 3/087 |
| | | | 327/205 |
| 2004/0215095 A1 | 10/2004 | Lee et al. | |

(Continued)

FOREIGN PATENT DOCUMENTS

| JP | 2004194908 | 7/2004 |
| KR | 1020060096842 | 9/2006 |
| WO | 2016000986 | 1/2016 |

OTHER PUBLICATIONS

International Search Report and Written Opinion for International Patent Application No. PCT/US2017/013801, dated Apr. 20, 2017.

(Continued)

*Primary Examiner* — Amanda Hulbert
*Assistant Examiner* — Natasha Patel
(74) *Attorney, Agent, or Firm* — Green, Howard & Mughal LLP

(57) ABSTRACT

Described is an apparatus which comprises: a current source to generate a current having AC and DC components; a current-to-voltage converter to convert the current or a copy of the current to a voltage proportional to a resistance, the voltage having AC and DC components that correspond to the AC and DC components of the current; a first sample-and-hold circuit to sample and filter the AC component from the voltage and to provide an output voltage with the DC component; a second sample-and-hold circuit to sample the output voltage; a voltage-to-current converter to convert the sampled output voltage to a corresponding current; and an amplifier to receive the output voltage.

10 Claims, 16 Drawing Sheets

(51) Int. Cl.
*H05B 33/08* (2006.01)
*A61B 5/00* (2006.01)

(56) References Cited

U.S. PATENT DOCUMENTS

| | | | |
|---|---|---|---|
| 2005/0025259 A1* | 2/2005 | Miyasita | H03K 5/003 375/319 |
| 2005/0187452 A1 | 8/2005 | Petersen et al. | |
| 2009/0110015 A1* | 4/2009 | Heink | B41J 2/473 372/38.02 |
| 2012/0098454 A1* | 4/2012 | Grotkowski | H05B 33/0815 315/246 |

OTHER PUBLICATIONS

Glaros, K. et al. "A Sub-mW Fully-Integrated Pulse Oximeter Front-End", IEEE Transactions on Biomedical Circuits and Systems, vol. 7, No. 3, Jun. 2013.

Hayes, M. et al. "A New Method for Pulse Oximetry Possessing Inherent Insensitivity to Artifact", IEEE Transactions on Biomedical Circuits and Systems, vol. 7, No. 3, Jun. 2013, pp. 452-461.

Patterson, J. et al."Ratiometric Artifact Reduction in Low Power Reflective Photoplethysmography" IEEE Transactions on Biomedical Circuits and Systems, vol. 7, No. 3, Jun. 2013, pp. 330-338.

Wong, A. et al. "A Low-Power CMOS Front-End for Photoplethysmographic Signal Acquisition With Robust DC Photocurrent Rejection", IEEE Transactions on Biomedical Circuits and Systems, vol. 2, No. 4, Dec. 2008, pp. 280-288.

Restriction Requirement for U.S. Appl. No. 14/752,881, dated Jul. 11, 2017.

Restriction Requirement dated Aug. 29, 2017 for U.S. Appl. No. 14/752,879.

International Preliminary Report on Patentability dated Sep. 7, 2018 for PCT Patent Application No. PCT/US17/13801.

Restriction Requirement from U.S. Appl. No. 14/752,879 dated Oct. 25, 2018, 7 pgs.

Restriction Requirement dated Oct. 25, 2018 for U.S. Appl. No. 14/752,881.

\* cited by examiner

APPARATUS AND METHOD FOR TRACKING AND CANCELLING DC OFFSET TO ACQUIRE SMALL AC SIGNAL USING DUAL FEEDBACK LOOPS

BACKGROUND

Photoplethysmography (PPG) based heart rate detection works by detecting reflected light from blood vessels as the blood vessels dilate and contract in sympathy with changing blood pressure associated with the heartbeat. The light is generated by a pulsed Light Emitting Diode (LED) which is placed against the skin (often a wrist) and detected by a photodiode also placed against the skin in near vicinity to the LED. Since the LED has a wide transmission angle and the emitted light is subject to scattering within the body, light reflects to the photodiode from extraneous sources such as bones as well as from the blood vessels. The signal component obtained from the light reflected from extraneous sources is commonly referred to as the DC component of the received signal. The undesired DC reflected component received is significantly greater than the signal from the blood vessel (e.g., the DC reflected component may be over 80 dB greater than the signal of interest which may typically be just 400 pA). The undesired DC component presents a number of issues. For example, amplifying the input signal to provide sufficient gain to the desired signal to detect it may lead to saturation in the amplifier stages of the PPG device.

PPG devices may wobble during use. As such, variable motion artifacts are introduced into the received photocurrents making tracking of the desired signal from the undesired signal difficult. One way to track the signal of interest from other undesirable received signals is to use a low gain, high bandwidth amplifier chain to avoid clipping (e.g., signal collapsing to ground), followed by an oversampling Analog-to-Digital Converter (ADC) (e.g., 22-bit ADC). This approach is brute-force and sub-optimal because it requires extra averaging and power burning.

BRIEF DESCRIPTION OF THE DRAWINGS

The embodiments of the disclosure will be understood more fully from the detailed description given below and from the accompanying drawings of various embodiments of the disclosure, which, however, should not be taken to limit the disclosure to the specific embodiments, but are for explanation and understanding only.

DETAILED DESCRIPTION

Figure 1:
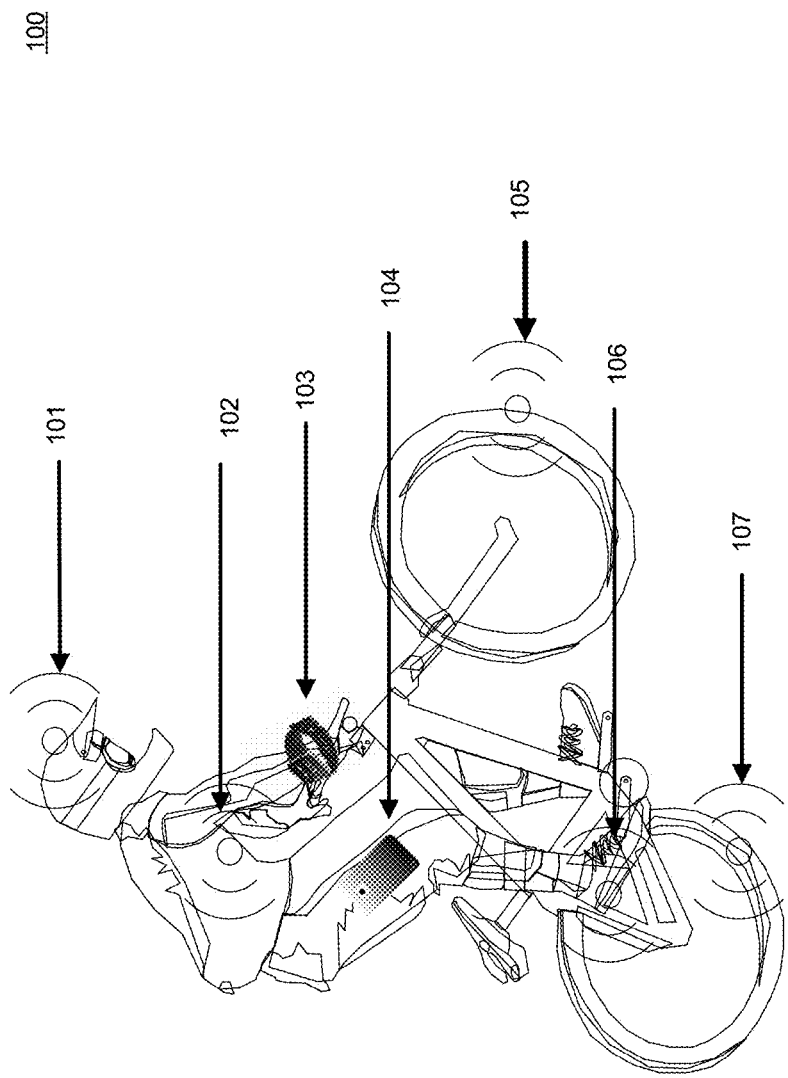
FIG. 1 illustrates an ensemble of wearable devices including a Photoplethysmography (PPG) device with apparatus to track and cancel DC offset using a linear feedback loop and a sampled feedback loop, according to some embodiments of the disclosure.

Market potential in the emerging wearable wellness and sports monitoring space is vast. Accurate integrated heart-rate and blood oxygen measurement circuitry is a vital part of increasing market share. A significant challenge for the present and the future is the fast and robust acquisition of cardiac waveforms from photodiodes using photoplethysmography or photoplethysmogram (PPG). PPG is an optically obtained volumetric measurement of an organ. Using traditional PPG measurement technology to wearable devices is non-optimal because they consume high power and circuit area. Additionally, wrist based wearable devices may introduce sharp motions due to user's wrist motion.

Some embodiments provide an apparatus and method to cancel the DC component, generated by the photodiode, by exploiting the DC component to generate a feedforward cancellation signal which is applied to an input of an amplifier (e.g., transimpedance amplifier (TIA) or an operation amplifier). In some embodiments, input offset current is sampled and converted to a feedforward offset voltage component. This feedforward offset voltage component is used to correct the DC component at the output of a TIA forming a first linear feedback loop of DC correction.

In some embodiments, to extend the dynamic range of the first linear feedback loop, a second feedback loop is introduced that includes a sample and hold circuit which works in clock antiphase to directly convert the feedforward offset voltage component back to a current, amplify it 'N' times (where 'N' is a number) and feed it back directly to the input in parallel with the efforts of the TIA. The result is a tandem offset cancellation circuit which possesses greatly enhanced dynamic range and can possess larger transimpedance gain as a result. In some embodiments, a large portion of DC offset is automatically provided through the high DC gain sampled feedback (e.g., the second feedback loop) and this is summated at a sensor interface with the fine grained lower current TIA feedback path (e.g., the first linear feedback loop). The net current feedback automatically and precisely tracks out DC offsets, in accordance with some embodiments.

Some embodiments describe an apparatus which comprises a current source (e.g., a photodiode) to generate a current having AC and DC components. In some embodiments, the apparatus comprises a current-to-voltage converter to convert the current or a copy of the current to a voltage proportional to a resistance. This voltage has AC and DC components that correspond to the AC and DC components of the current provided by the current source. In some embodiments, the apparatus comprises a first sample-and-hold circuit to sample and filter the AC component from the voltage and to provide an output voltage (i.e., Vref) with the DC component.

In some embodiments, the apparatus comprises a second sample-and-hold circuit to sample the output voltage Vref. In some embodiments, the apparatus comprises a voltage-to-current converter to convert the sampled output voltage to a corresponding current. In some embodiments, the apparatus comprises an amplifier (e.g., TIA) to receive the output voltage, where the amplifier is part of first linear feedback loop while the second sample-and-hold circuit and the voltage-to-current converter are part of a second sampling feedback loop.

There are many technical effects of various embodiments. For example, the apparatus of various embodiments have comparatively smaller area than traditional PPG devices and is simpler in operation. The apparatus of some embodiments do not inherently use external digital control signals or data converters to condition the received input signal. The apparatus of some embodiments adapt to DC offset in real-time. The apparatus of some embodiments is a low noise apparatus with self-filtering. The apparatus of various embodiments consumes much lower power than traditional PPG devices. The apparatus of some embodiments are substantially insensitive to process or leakage issues and may not use trimming. The offset cancellation circuit of various embodiments possesses greatly enhanced dynamic range and can possess larger transimpedance gain (compared to as an offset cancellation circuit with only a linear feedback feedforward path). Other technical effects will be evident by the description of various embodiments.

In the following description, numerous details are discussed to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, in order to avoid obscuring embodiments of the present disclosure.

Note that in the corresponding drawings of the embodiments, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary embodiments to facilitate easier understanding of a circuit or a logical unit. Any represented signal, as dictated by design needs or preferences, may actually comprise one or more signals that may travel in either direction and may be implemented with any suitable type of signal scheme.

Throughout the specification, and in the claims, the term "connected" means a direct connection, such as electrical, mechanical, or magnetic connection between the things that are connected, without any intermediary devices. The term "coupled" means a direct or indirect connection, such as a direct electrical, mechanical, or magnetic connection between the things that are connected or an indirect connection, through one or more passive or active intermediary devices. The term "circuit" or "module" may refer to one or more passive and/or active components that are arranged to cooperate with one another to provide a desired function. The term "signal" may refer to at least one current signal, voltage signal, magnetic signal, or data/clock signal. The meaning of "a," "an," and "the" include plural references. The meaning of "in" includes "in" and "on."

The terms "substantially," "close," "approximately," "near," and "about," generally refer to being within +/−10% of a target value. Unless otherwise specified the use of the ordinal adjectives "first," "second," and "third," etc., to describe a common object, merely indicate that different instances of like objects are being referred to, and are not intended to imply that the objects so described must be in a given sequence, either temporally, spatially, in ranking or in any other manner.

For purposes of the embodiments, the transistors in various circuits, modules, and logic blocks are metal oxide semiconductor (MOS) transistors, which include drain, source, gate, and bulk terminals. The transistors also include Tri-Gate and FinFET transistors, Gate All Around Cylindrical Transistors, Tunneling FET (TFET), Square Wire, or Rectangular Ribbon Transistors or other devices implementing transistor functionality like carbon nano tubes or spintronic devices. MOSFET symmetrical source and drain terminals i.e., are identical terminals and are interchangeably used here. A TFET device, on the other hand, has asymmetric Source and Drain terminals. Those skilled in the art will appreciate that other transistors, for example, Bi-polar junction transistors—BJT PNP/NPN, BiCMOS, CMOS, eFET, etc., may be used without departing from the scope of the disclosure.

FIG. 1 illustrates ensemble 100 of wearable devices including a PPG device with apparatus to track and cancel DC offset using a linear feedback loop and a sampled feedback loop, according to some embodiments of the disclosure. In this example, ensemble 100 is on a person and his/her ride (here, a bicycle). However, the embodiments are not limited to such. Other scenarios of wearable devices and their usage may work with the various embodiments.

For example, PPG device with apparatus to track and cancel DC offset can be embedded into some other products (e.g., medical devices, ambulances, patient uniform, doctor's uniform, etc.) and can be controlled using a controller or a terminal device. The PPG device with apparatus to track and cancel DC offset of some embodiments can also be part of a wearable device. The term "wearable device" (or wearable computing device) generally refers to a device coupled to a person. For example, devices (such as sensors, cameras, speakers, microphones (mic), smartphones, smart watches, medical devices, etc.) which are directly attached on a person or on the person's clothing are within the scope of wearable devices.

In some examples, wearable computing devices may be powered by a main power supply such as an AC/DC power outlet. In some examples, wearable computing devices may be powered by a battery. In some examples, wearable computing devices may be powered by a specialized external source based on Near Field Communication (NFC). The specialized external source may provide an electromagnetic field that may be harvested by circuitry at the wearable computing device. Another way to power the wearable computing device is electromagnetic field associated with wireless communication, for example, WLAN (Wireless Local Area Network) transmissions. WLAN transmissions use far field radio communications that have a far greater range to power a wearable computing device than NFC transmission. WLAN transmissions are commonly used for wireless communications with most types of terminal computing devices.

For example, the WLAN transmissions may be used in accordance with one or more WLAN standards based on Carrier Sense Multiple Access with Collision Detection (CSMA/CD) such as those promulgated by the Institute of Electrical Engineers (IEEE). These WLAN standards may be based on CSMA/CD wireless technologies such as Wi-Fi™ and may include Ethernet wireless standards (including progenies and variants) associated with the IEEE 802.11-2012 Standard for Information technology—Telecommunications and information exchange between systems—Local and metropolitan area networks—Specific requirements Part 11: WLAN Media Access Controller (MAC) and Physical Layer (PHY) Specifications, published March 2012, and/or later versions of this standard ("IEEE 802.11").

Continuing with the example of FIG. 1, ensemble 100 of wearable devices includes device 101 (e.g., camera, microphone, etc.) on a helmet, device 102 (e.g., PPG device with apparatus to track and cancel DC offset, where the PPG device can be a pulse sensor, heartbeat sensor, blood oxygen level sensor, blood pressure sensor, or any other sensor such as those used in the fields of ECG (electrocardiography), EMG (electromyography), EOG (electrooculography, which is a detection of current associated with movement of the eyeball), ENG (electronystagmography), etc.) on the person's arm, device 103 (e.g., a smart watch that can function as a terminal device, controller, or a device to be controlled), device 104 (e.g., a smart phone and/or tablet in a pocket of the person's clothing), device 105 (e.g., pressure sensor to sense or measure pressure of a tire, or gas sensor to sense nitrogen air leaking from the tire), device 106 (e.g., an accelerometer to measure paddling speed), device 107 (e.g., another pressure sensor for the other tire). In some embodiments, ensemble 100 of wearable devices has the capability to communicate by wireless energy harvesting mechanisms or other types of wireless transmission mechanisms.

In some embodiments, device 102 comprises PPG device with apparatus to track and cancel DC offset. In some embodiments, in a PPG application, a light source (e.g., a LED) shines light into a user's skin under a wearable device (e.g., a smartwatch). In some embodiments, this light is shone at low duty cycles to save power (i.e., a short duration pulse to minimise power dissipation). Duty cycle is the ratio of on to off events (i.e., ratio of logic 1 to logic 0 etc.). The repetition rate of the pulse may be a few tens of Hertz to up to a few kHz, in accordance with some embodiments. A person skilled in the art would appreciate that the higher the frequency (e.g., the repetition rate of the pulse) the better the resolution but the more the current consumed.

In some embodiments, the PPG device comprises a current-source that activates by light (e.g., photodiode) which generates an output current in response to the received light, where the output current has both the desired AC component and the undesired component such as DC plus motion artifacts. Generally, the DC component is less than 0.5 Hz and the desired AC component is in the range of 0.5 Hz to 20 Hz (e.g., the frequency of blood modulation under the skin). However, the embodiments are applicable to other values of AC and DC components.

The received light is the light reflected or scattered off the bones and/or blood vessels under the user's skin. In some embodiments, the received light is detected by a photodetector in a narrow pulsed time window and is then conditioned, amplified, and converted to a digital signal so digital signal processing can be applied and the heartrate and/or other data can be extracted. In some embodiments, the PPG device includes a current-to-voltage (I-to-V) converter which receives the output current from the photodiode, and generates an output voltage proportional to the input current (i.e., current from the photodiode). In some embodiments, the output voltage is inversely proportional to the input current. More current may imply a greater amplitude output signal though there may be an inversion in sense.

The output voltage has AC and DC components that correspond to the AC and DC components of the current provided by the photodiode. In some embodiments, a first sample-and-hold (or a track and hold) circuit and filter is used to remove the AC component from the output voltage and to store the DC component. In some embodiments, the apparatus comprises a second sample-and-hold circuit to sample the voltage output from the first sample-and-hold (or a track and hold) circuit and filter. In some embodiments, the apparatus comprises a voltage-to-current converter to convert the sampled output voltage to a corresponding current. In some embodiments, the apparatus comprises an amplifier to receive the voltage output of the first sample-and-hold (or a track and hold) circuit and filter, where the amplifier is part of first linear feedback loop while the second sample-and-hold circuit and the voltage-to-current converter are part of a second sampling feedback loop.

In some embodiments, this stored DC component (e.g., stored in a switching capacitor of the first sample and hold circuit) becomes a reference voltage for the amplifier configured as a transimpedance amplifier (TIA). As such, the undesired DC component is exploited to generate a feedforward cancellation signal which is applied to the non-inverting input of the TIA, and so the DC offset is cancelled at the output and moved instead to the input.

In some embodiments, the PPG device includes another voltage-to-current converter which establishes the TIA output at the level of the DC component. As such, slewing in the TIA is reduced upon receiving a next pulse of current from the photodiode. Various embodiments here are described with reference to the amplifier being a TIA. However, other implementations are also possible.

In some embodiments, the PPG device includes an antenna to transmit the processed data (e.g., the digitized data in modulated form from the output of the TIA) to a controller or a terminal device (e.g., a smart phone, laptop, cloud, etc.) for further processing. In some embodiments, the antenna may comprise one or more directional or omni-directional antennas, including monopole antennas, dipole antennas, loop antennas, patch antennas, microstrip antennas, coplanar wave antennas, or other types of antennas suitable for transmission of Radio Frequency (RF) signals. In some multiple-input multiple-output (MIMO) embodiments, the antennas are separated to take advantage of spatial diversity.

Figure 2:
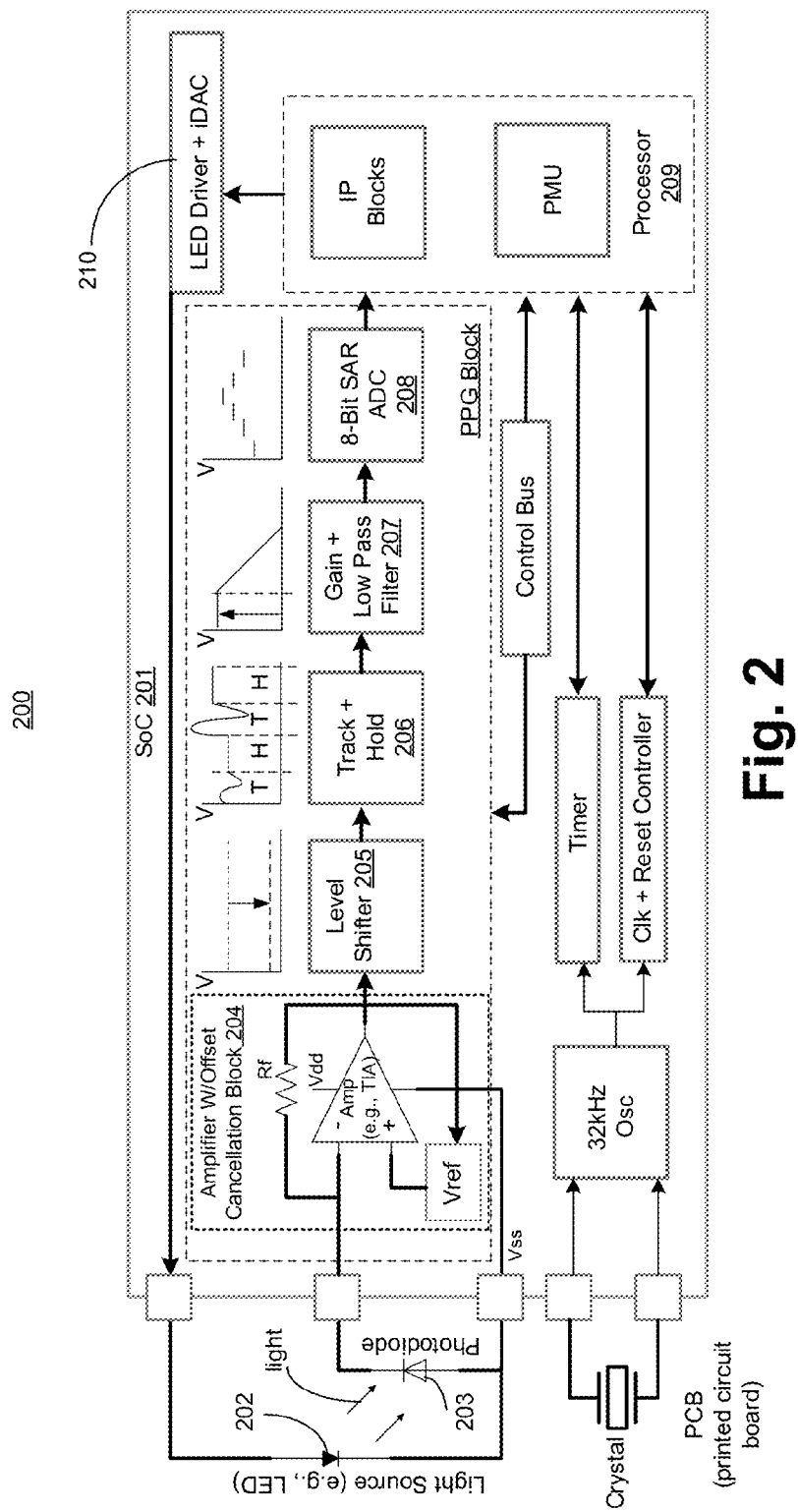
FIG. 2 illustrates a SoC (System-on-Chip) with a PPG device with apparatus to track and cancel DC offset using a linear feedback loop and a sampled feedback loop, according to some embodiments of the disclosure.

FIG. 2 illustrates apparatus 200 with a SoC (System-on-Chip) with a PPG device with apparatus to track and cancel DC offset using a linear feedback loop and a sampled feedback loop, according to some embodiments of the disclosure. In some embodiments, apparatus 200 is part of a wearable device (e.g., a smartwatch). In some embodiments, apparatus 200 comprises SoC 201, light source (e.g., LED) 202, current-source (e.g., photodiode) 203, Amplifier with Offset Cancellation Block 204, Level Shifter 205, Track and Hold circuit 206, Amplifier (i.e., Gain stage) and Low Pass Filter (LPF) 207, Analog-to-Digital Converter (ADC) 208, Processor 209, LED Driver and current Digital-to-Analog Converter (iDAC) 210, Crystal for providing a periodic clock signal, Oscillator, Timer, Clock (Clk) and Reset Controller, and Control Bus as shown. Apparatus 200 may have fewer or more components than does listed here.

The term "light source" generally refers to a source that may provide visible light (i.e., visible to human eye and having wavelengths in the range of 400 nm to 700 nm) or invisible light (i.e., invisible to human eye and having wavelengths outside the range of 400 nm to 700 nm).

Various embodiments here are described with reference to the amplifier in Block 204 being a TIA. However, other implementations of the amplifier are also possible. Various embodiments here are described with reference to the light source being an LED. However, other implementations of the light source are also possible. Various embodiments here are described with reference to the current-source in being a photodiode. However, other implementations of the current-source are also possible.

In some embodiments, current (e.g., LED current) is driven by the light source (e.g., LED driver) in response to controls provided by Processor 209. For example, the controls provided by Intellectual Property (IP) block(s), of Processor 209, for the LED driver may set the Pulse Repetition Frequency (PRF), light intensity, duty cycle ratio, and other attributes of LED 202. In some embodiments, the PRF of LED 202 is set low (e.g., several Hertz). In some embodiments, the duty cycle ratio is also set low (e.g., 100:1). For example, the off-time of LED 202 has a longer duration than the on-time of LED 202. In some embodiments, this control timing scheme of LED 202 allows to conserve power because LED 202 consumes hundreds of milli-Amperes (mA). In some embodiments, photodiode 203 is an off-chip diode which receives the light reflected off the user's wrist. In some embodiments, photodiode 203 is integrated in SoC 201 such that it is able to receive light.

In some embodiments, the current generated by photodiode 203 is received by Amplifier Block 204. For example, the current corresponding to the pulsed light transmitted by LED 202 and reflected off from the organs or bones of the user's wrist is received by Amplifier Block 204. In some embodiments, Amplifier Block 204 removes the DC offset present from the received signal using schemes described with reference to FIGS. 3-10.

Referring back to FIG. 2, Amplifier Block 204 generates a voltage output which is level shifted down to a suitable common mode and held between pulses of LED 202 by Track and Hold Filter 206. Any suitable circuit can be used for implementing Track and Hold Filter 206. The output of Track and Hold Filter 206 are stripped-out AC waveforms (e.g., portions of the AC waveforms), according to some embodiments. In some embodiments, the output of Track and Hold Filter 206 are presented to an active second order low pass filter (e.g., Gain and Low Pass Filter 207). In some embodiments, Gain and Low Pass Filter 207 includes an amplifier to amplify the output of Track and Hold Filter 206 and to filter the high frequency AC component from the output. In some embodiments, Gain and Low Pass Filter 207 has enough gain to excite ADC 208. In some embodiments, ADC 208 is a Successive Approximation Register (SAR) based ADC.

SAR based ADC 208 is a type of ADC that converts a continuous analog waveform (e.g., filtered output of Gain and Low Pass Filter 207) into a discrete digital representation via a binary search through all possible quantization levels before finally converging upon a digital output for each conversion. In some embodiments, ADC 208 is designed such that poles are placed to limit aliasing. In some embodiments, ADC 208 is 8-bit SAR topology sampling at around 100 Hz and using around 20 dB of gain after trans-impedance of about 1.8 MegR. In other embodiments other types of ADCs may be used to digitize the filtered content from Gain and Low Pass Filter 207.

In some embodiments, ADC 208 is switched on to sample the signal presented by the chain (e.g., blocks 203, 204, 205, 206, and 207) when LED 202 is pulsed on. In some embodiments, the entire system can be shut down between LED on phases to conserve battery power. For example, when LED 202 is off, the detection mechanism having Amplifier Block 204 along with other components may be turned off to conserve power. In some embodiments, the DC information required to track the signal at the next on-phase is held on integrated MOS capacitors. In some embodiments, the capacitor(s) is an external capacitor (e.g., external to the die). For example, the capacitor may be positioned on a package of the die. Here, leakage may not be a major concern with this system as merely small portions of the large DC levels held may leak away, and not the signal of interest itself.

In some embodiments, Processor 209 processes the output of ADC 208 to generate a result (e.g., heartbeat, pulse rate, blood pressure, etc.). In some embodiments, Processor 209 may include Power Management Unit (PMU) to manage the power consumption of various blocks of SoC 201. In some embodiments, Processor 209 includes a plurality of Intellectual Property (IP) Blocks such as caches, memory controller, register files, input-output circuits, execution units, etc. In some embodiments, Processor 209 controls various attributes of LED 202, such as the strength of light generated by LED 202, by controlling LED Driver and current DAC (iDAC) 210.

In some embodiments, a 32 kHz oscillator (osc) is provided to illustrate the low clock frequency uses of this circuitry (and therefore low power). In some embodiments, Timer/reset controller are generic features associated with a generated clock. In some embodiments, the control bus is intended to be a digital interface between Processor 209 and the PPG Block. In some embodiments, the Control Bus can be used to trim values, control lines, and/or enables, any form of logic level information that may be passed to and from the PPG Block.

Figure 3:
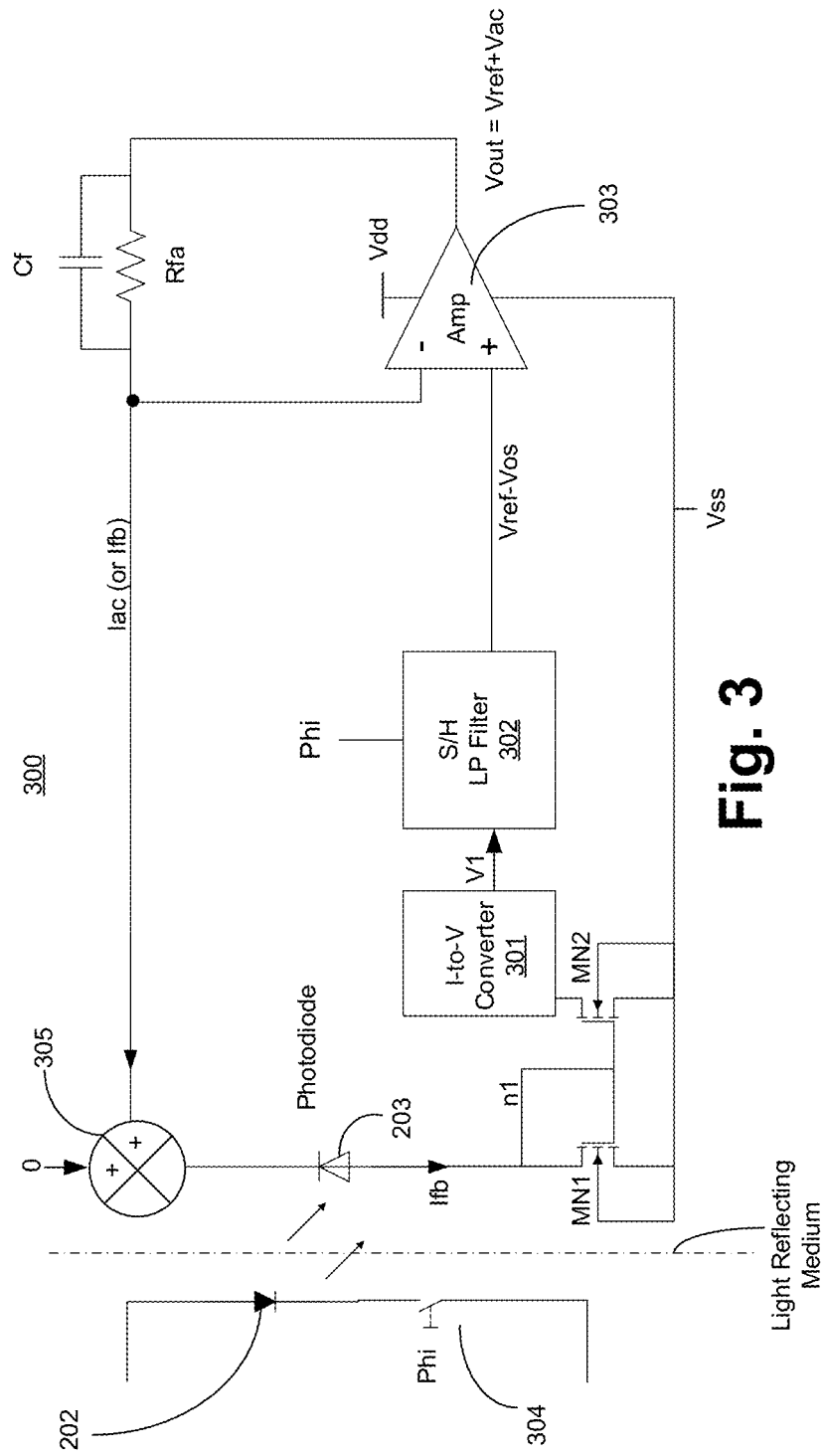
FIG. 3 illustrates a front-end of the PPG device with a DC offset reducing mechanism having a linear feedback loop, according to some embodiments of the disclosure.

FIG. 3 illustrates front-end 300 of the PPG device with a DC offset reducing mechanism having a linear feedback loop, according to some embodiments of the disclosure. It is pointed out that those elements of FIG. 3 having the same reference numbers (or names) as the elements of any other figure can operate or function in any manner similar to that described, but are not limited to such.

In some embodiments, front-end 300 comprises light source 202, current-source 203, current mirror having n-type transistors MN1 and MN2, I-to-V Converter 301, Sample and Hold Low Pass Filter (S/H LP Filter) 302, amplifier 303, LED on/off switch 304, feedback resistor Rfa, and compensation capacitor Cf.

Various embodiments here are described with reference to amplifier 303 as being a TIA (hence, TIA 303). However, other implementations of amplifier 303 are also possible. In some embodiments, amplifier 303 has a single output (as shown in FIG. 3). In some embodiments, amplifier 303 has dual outputs (e.g., shown as Amplifier 803 in FIG. 8). Various embodiments here are described with reference to light source 202 in being an LED (hence, LED 202). However, other implementations of light source 202 are also possible. Various embodiments here are described with reference to current-source 203 being a photodiode (hence, photodiode 203). However, other implementations of current-source 203 are also possible.

In some embodiments, pulsed current generated by photodiode 203 is mirrored by diode connected transistor MN1 to transistor MN2. In some embodiments, the current generated by photodiode 203 is pulsed by switch 304 which is controlled by control signal Phi. In some embodiments, Phi is a clock signal with periodic high and low pulses. In some embodiments, when Phi is logic high (e.g., first phase or high phase), switch 304 is closed allowing LED 202 to shine light on the light reflecting medium (e.g., wrist of a user). In some embodiments, when Phi is logic low (e.g., second phase or low phase), switch 304 is off which causes LED 202 to be off.

In some embodiments, I-to-V Converter 301 receives current from transistor MN2 and converts that current to a corresponding voltage. As such, the current is sampled from photodiode 203 and used for feed-forward DC offset cancellation at the input stage of TIA 303. In some embodiments, the output voltage from I-to-V Converter 301 is scaled to a proportional-to-Rfa voltage, where Rfa is a resistance of a resistive device (e.g., passive resistor or transistor configured as a resistor) which is the same as the resistance of feedback resistor Rfa of TIA 303. In some embodiments, the output voltage from I-to-V Converter 301 is inversely proportional to the input current (i.e., current through transistor MN2). The output voltage has an AC component (which is the desirable signal) and a DC component (which may be the undesirable signal).

In some embodiments, the output voltage (i.e., the output of I-to-V Converter 301) is sampled and then held by S/H LP Filter 302. In some embodiments, S/H LP Filter 302 removes the AC component and stores the DC component in a capacitive device (e.g., a MOS based capacitor or any other type of capacitor). In some embodiments, the low pass filter of S/H LP Filter 302 filters the AC component (of the output voltage from I-to-V Converter 301) using an RC (resistor-capacitor) filter which can both sample and hold its output. One implementation of S/H LP Filter 302 is a switched capacitor and a resistor. In some embodiments, a MOS based capacitor or any other type of capacitor coupled in series with a switch is used to implement the switched capacitor. In some embodiments, the resistor of the S/H LP Filter 302 is a MOS based resistance (e.g., a transistor operating in the linear region).

In some embodiments, the output voltage is sampled when Phi is logic high (e.g., when LED 202 is on). In some embodiments, the output DC component of S/H LP Filter 302 is an output voltage which is to function as a reference voltage for TIA 303. As such, the reference voltage is Vref-Vos which is provided to TIA 303, where "Vref-Vos" indicates that this signal is a reference level (e.g., Vref=Iref*Rfa) less the offset Voltage (Vos) representing the offset current (e.g., Iphotodiode*Rfa). In some embodiments, I-to-V Converter 301 causes the output voltage (e.g., the DC component held by S/H LP Filter 302) to lower in voltage level as the DC component of the input current increases (e.g., as the current generated by photodiode 203 increases).

In some embodiments, TIA 303 has an inverting input and a non-inverting input. In some embodiments, a voltage is applied to the non-inverting input while the inverting input is set by a current sum to zero via resistor Rfa and photodiode 203 paths. In some embodiments, the output of S/H LP Filter 302 is provided to the non-inverting input of the input stage of TIA 303 in order to bring its output back down to the desired common mode level. TIA 303 is a current-to-voltage converter that converts current Iac (or Ifb) from photodiode 203 to an output voltage Vout relative to a reference voltage. The gain of TIA 303 depends on the feedback resistor having resistance Rfa.

In some embodiments, amplifier 303 is implemented as an operational amplifier which is configured as a TIA. One reason for using TIA 303 with a current-source sensor like photodiode 203 is that photodiode 203 has a current response which is more linear than a voltage response. In some embodiments, TIA 303 presents a low impedance to photodiode 203 and isolates it from the output voltage Vout of TIA 303 via resistor Rfa. In some embodiments, a compensation capacitor Cf is added in parallel to resistor Rfa to provide stability to the feedback loop from the output of TIA 303 to its inverting input. In some embodiments, the apparatus of various embodiments can be combined with a bootstrapping technique (e.g., Design Note 399 from Linear Technology Corporation of California) to reduce stability dependence on photodiode capacitance.

In some embodiments, photodiode current Iac (of Ifb) is simultaneously sensed in a separate parallel path (through the inverting input of TIA 303). In some embodiments, a copy of the photodiode current seen in feedback resistor Rfa is provided by a dual output stage amplifier 303, and this duplicate photodiode current is then subtracted from a reference current and the resultant current is then pushed through a duplicate resistor Rfa (shown in FIGS. 8, 9, and 10).

Figure 7:
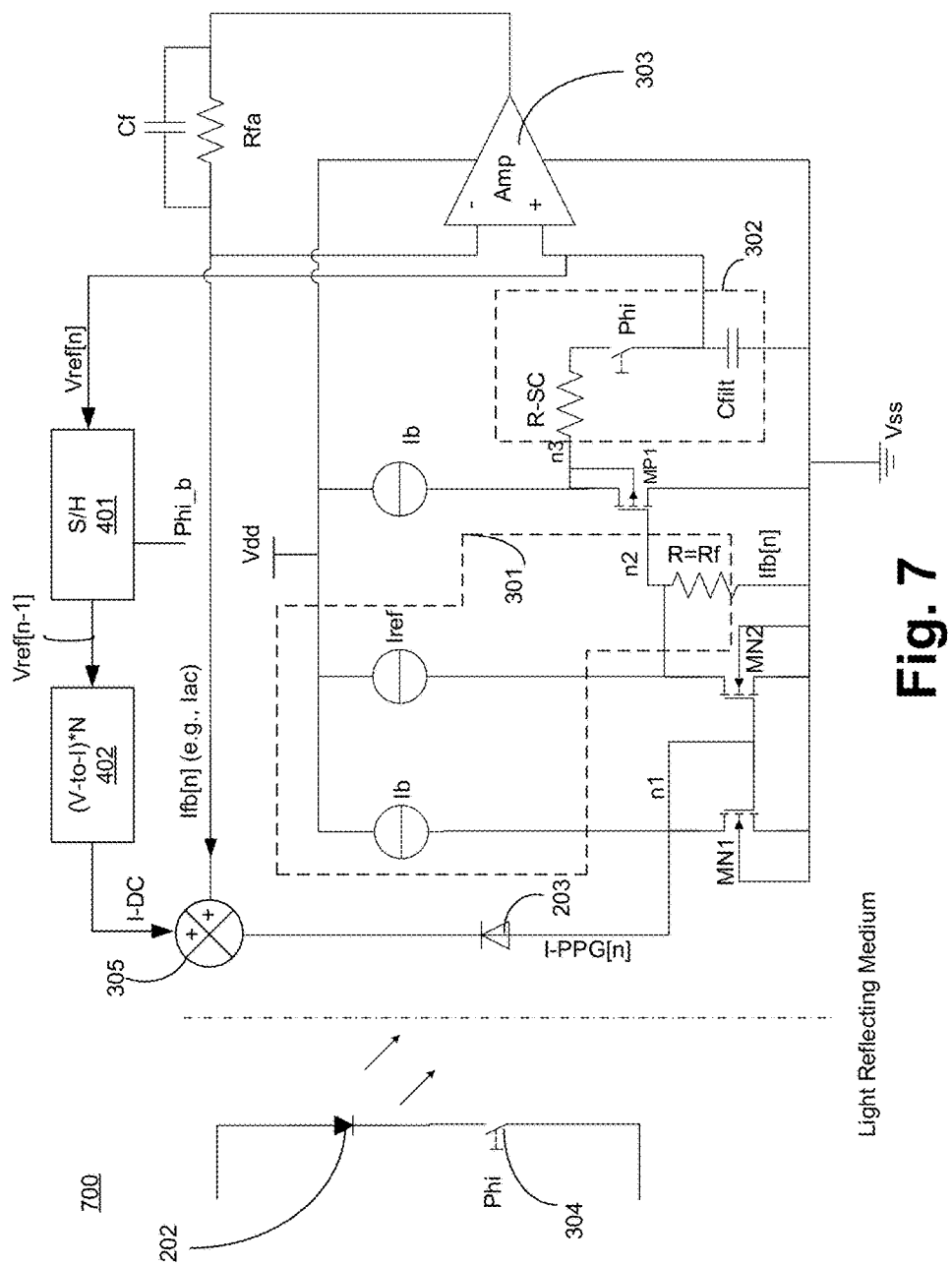
FIG. 7 illustrates an apparatus showing a transistor-level feedforward path coupled to the non-inverting input of the amplifier, and a sampled feedback loop, according to some embodiments of the disclosure.

Referring back to FIG. 3, in some embodiments, the output voltage of I-to-V Converter 301 is level shifted up and buffered by a transistor (e.g., a p-type transistor). One such implementation is shown in FIG. 7. Referring back to FIG. 3, in some embodiments, the buffered voltage is filtered with a large time constant using an on-die (or off die) capacitor and a resistor and fed forward to the non-inverting input of TIA 303. In some embodiments, the on-die capacitor and the resistor are part of the S/H LP Filter 302.

In some embodiments, because the DC current was subtracted from a reference at summing node 305 and then undergone the same impedance conversion as Vout through resistor Rfa, the DC level at the non-inverting input of TIA 303 is brought down. As such, the DC level at the output of TIA 303 is lowered, and the offset is cancelled. In some embodiments, if the feedforward pole is suitably low, the AC component passes through TIA 303.

Figure 4A:
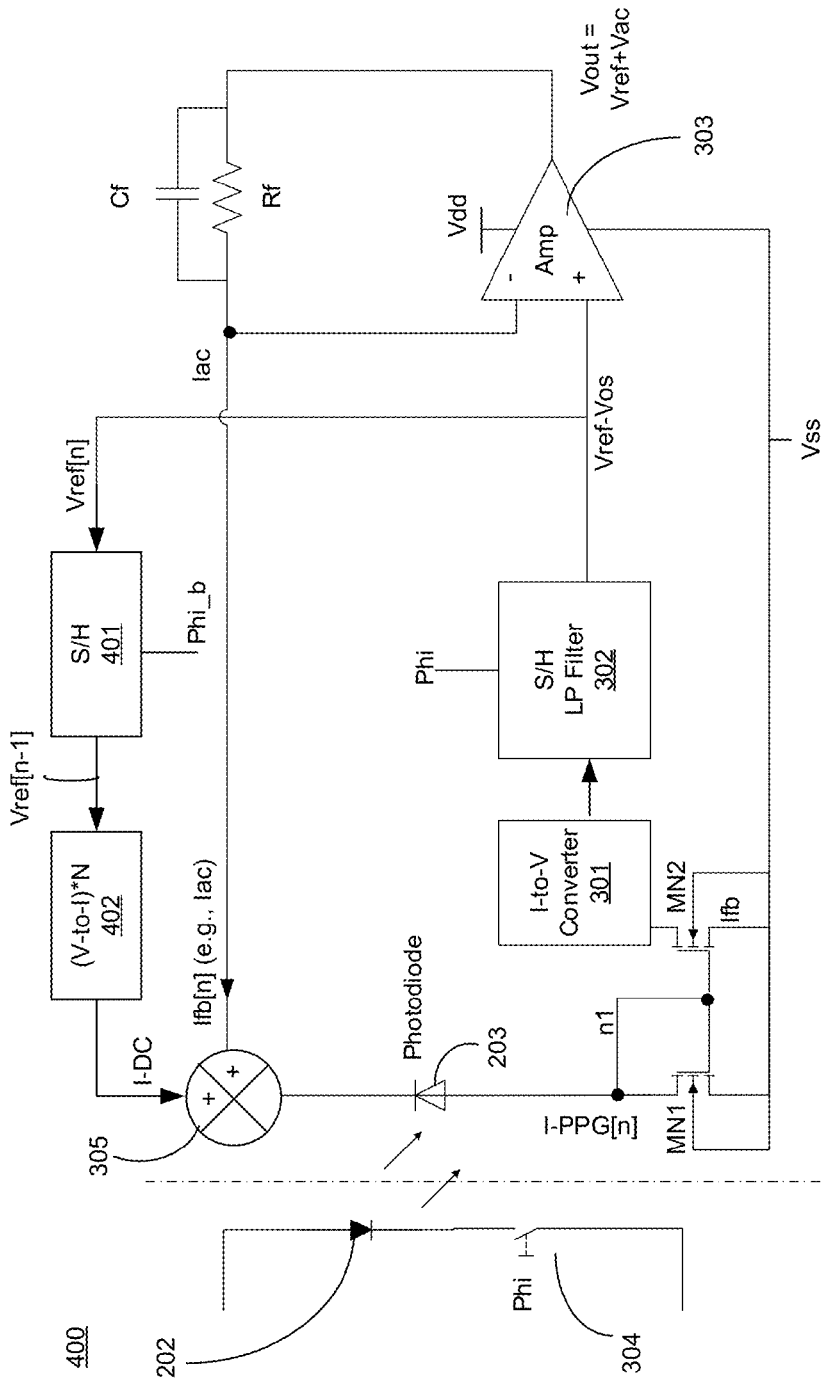
FIG. 4A illustrates a front-end of the PPG device with apparatus to track and cancel DC offset using a linear feedback loop and a sampled feedback loop, according to some embodiments of the disclosure.

FIG. 4A illustrates front-end 400 of the PPG device with apparatus to track and cancel DC offset using a linear feedback loop and a sampled feedback loop, according to some embodiments of the disclosure. It is pointed out that those elements of FIG. 4 having the same reference numbers (or names) as the elements of any other figure can operate or function in any manner similar to that described, but are not limited to such. So as not to obscure the embodiments, differences between FIG. 4A and FIG. 3 are described.

Front-end 400 is similar to front-end 300 except that a second sample and hold (S/H) circuit 401 and voltage-to-current (V-to-I) Converter 402 are added as shown. In some embodiments, second S/H circuit 401 samples the output (Vref-Vos) of first S/H LP Filter 302 at a second phase of Phi (i.e., Phi_b) while first S/H LP Filter 302 samples the output of I-to-V Converter 301 at a first phase of Phi.

In some embodiments, during the off period of LED 202, second S/H circuit 401 is activated (because Phi_b is high, which is an inverse of Phi). In this example, Phi is low to turn off LED 202 and high to turn on LED 202. However, the logic can be inversed to achieve the same effect without changing the essence of various embodiments. In one such embodiment, the DC voltage on the filter capacitor of S/H LP Filter 302 is converted to DC offset current component (Iac) present at the inverting input of TIA 303 when LED 202 was on. In some embodiments, output Vref[n−1] of S/H circuit 401 is converted to a corresponding DC current I-DC by V-to-I Converter 402. This DC current is added to Iac to cancel any additional offset in current I-PPG[n] (which is the photodiode current), in accordance with some embodiments.

Apparatus 400 illustrates two feedback paths, in accordance with some embodiments. In some embodiments, the first feedback path or loop is a linear feed-forward loop that allows for continuous fine grained DC correction. The first loop is generally described as linear because when Phi is '1' it is essentially an RC filter. However, when Phi is '0', the linear loop is broken and the result is held so the first loop is pseudo-linear in that case. This loop applies a scaled voltage representation of the DC component of the photodiode current (I-PPG[n]) to make continuous time changes to TIA output Vout (e.g., during being Phi '1'). In some embodiments, the first feedback path or loop starts from Photodiode 203 and includes the current mirror (having transistors MN1 and MN2), I-to-V Converter 301, S/H LP Filter 302, Amplifier 303, Resistor Rf (same as Rfa), and summing node 305.

In some embodiments, the second feedback loop is a sampled feedback path. The second feedback loop samples the offset voltage and then converts back the sampled offset voltage to current and gained N times as I-DC. I-DC is then summed at summing node 305. As such, the second feedback path or loop starts from Photodiode 203 and includes the current mirror (having transistors MN1 and MN2), I-to-V Converter 301, S/H LP Filter 302, S/H circuit 401, V-to-I Converter 402, and summing node 305. I-DC in conjunction to Iac (or Ifb[n]) supports Amplifier 303 to reduce the DC offset. The second loop is characterized as sampled as it merely samples a static voltage (Vref) and converts it to a current which it dumps back into the diode, in accordance with some embodiments.

Referring to common circuitry in FIG. 3 and FIG. 4A, the pulsed input current I-PPG[n] (e.g., small AC riding on large DC levels) is converted to a voltage through a resistor Rf via TIA 303. The output Vout of TIA 303 conveys a large DC voltage level and a small AC voltage. The diode current I-PPG[n] is also simultaneously sensed with a current mirror in a separate parallel path, subtracted from a reference current and then converted to a voltage using the same value Rf in I-to-V 301. This voltage is then filtered and sampled by S/H LP 302 with a large time constant using an on-chip/off-chip capacitor and a resistor element (e.g., a switched capacitor or a weak inversion tunable MOS device) and fed forward to the non-inverting input of TIA 303.

Because the DC current is subtracted from a reference and then undergone the same impedance conversion as Vout through Rf, it serves to correctly bring down the DC level at the non-inverting input and therefore the DC level at the TIA output Vout, removing the offset, according to some embodiments. In some embodiments, the AC component is free to pass provided the feed forward pole is low enough.

With the additional circuitry (e.g., S/H 401 and V-to-I Converter 402) of FIG. 4A, in some embodiments during the off-period of the LED (e.g., when Phi_b is logically high and Phi is logically low), S/H circuit 401 and (V-to-I)*N 402 converts the DC voltage on the capacitor of S/H LP filter 302 and uses it to recreate the DC offset current component in I-PPG[n] present at the input of TIA 303 when the LED 202 was on. In some embodiments, this current is amplified N times by V-to-I Converter 402 and injected back into photodiode 203, in parallel with Ifb, as I-DC.

Mathematically, the currents and voltages can be described as follows:

$$I\text{-}DC = N \cdot Ifb[n-1] \qquad \text{eq. 1}$$

$$I\text{-}PPG[n] = N \cdot Ifb[n-1] + Ifb[n] \qquad \text{eq. 2}$$

$$\text{then, } Ifb[n] = I\text{-}PPG[n]/(1+N) \qquad \text{eq. 3}$$

Assuming the system has settled out so the sample to sample feedback current is equal: i.e. $Ifb[n-1] = Ifb[n]$ $$V1[n] = (Iref - Ifb[n]) \cdot Rf \qquad \text{eq. 4}$$

$$Vref[n] = V1[n]/(1+sT) \qquad \text{eq. 5}$$

$$Ifb[n] = (Iref - I\text{-}PPG[n]/(1+N))/(1+sT) \qquad \text{eq. 6}$$

Eq. 6 shows the response of Ifb (e.g., current through TIA Rfa) to the non-inverting input of amplifier 303. The low pass filter ensures the signal is a DC component merely, in accordance with some embodiments. The (1+N) on the denominator shows that the feedback current required through Rf at steady state has been reduced by a design factor 1+N.

In some embodiments, after a few samples of I-PPG[n], apparatus 400 will now self-regulate itself to provide a much larger DC offset correction component directly to photodiode 203 via the second feedback loop path and leave a much smaller component via TIA 303. This allows the linear correction range to be greatly enhanced and the gain of TIA 303 to be increased significantly. The current I-DC provided by the second feedback loop allows a higher value of resistance for resistor Rf, in accordance with some embodiments. The current I-DC provided by the second feedback loop increases the tolerance of DC offset, in accordance with some embodiments.

Figure 4B:
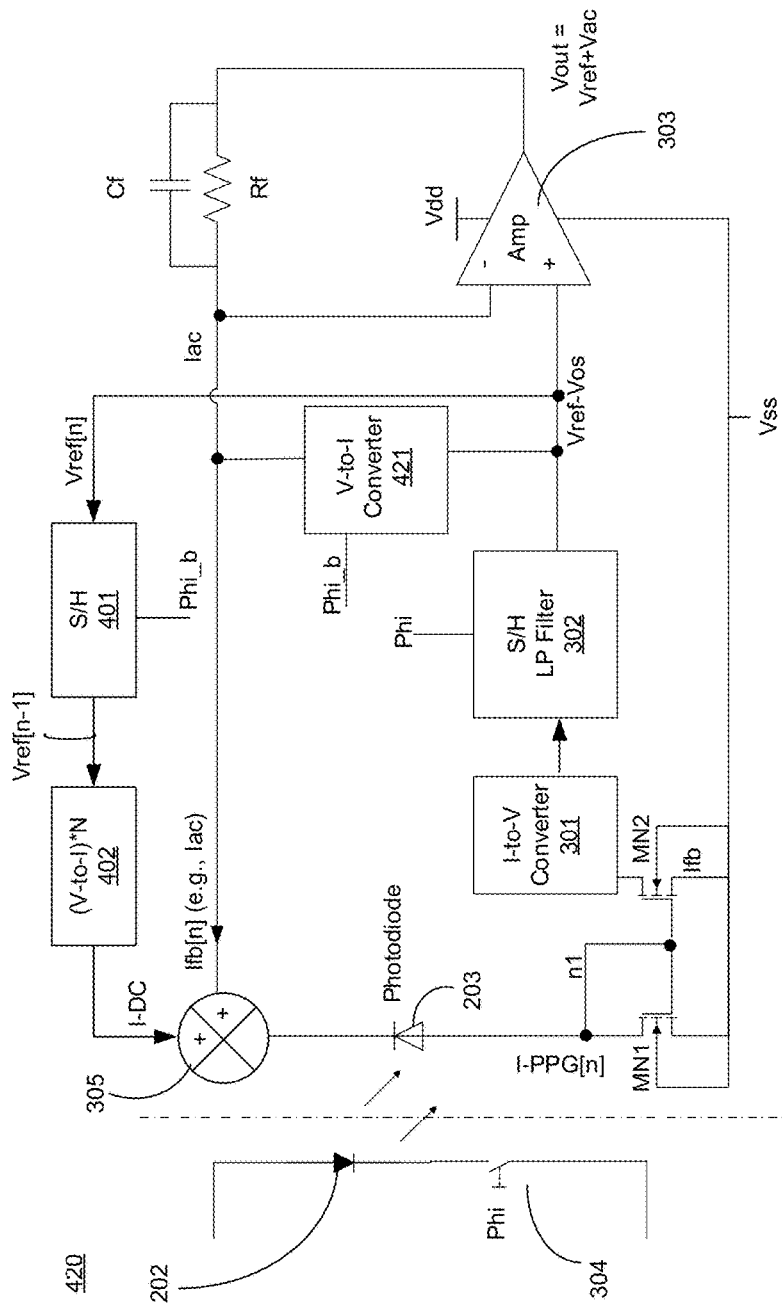
FIG. 4B illustrates a front-end of the PPG device with apparatus to track and cancel DC offset using a linear feedback loop and a sampled feedback loop, according to some embodiments of the disclosure.

FIG. 4B illustrates front-end 420 of the PPG device with apparatus to track and cancel DC offset using a linear feedback loop and a sampled feedback loop, according to some embodiments of the disclosure. It is pointed out that those elements of FIG. 4B having the same reference numbers (or names) as the elements of any other figure can operate or function in any manner similar to that described, but are not limited to such. So as not to obscure the embodiment of FIG. 4B, differences between FIG. 4A and FIG. 4B are described.

Front-end 420 is similar to front-end 400 except that a voltage-to-current (V-to-I) Converter 421 is added as shown. In some embodiments, V-to-I Converter 421 establishes the output of TIA 303 at the DC level such that slewing in TIA 303 is reduced when receiving the next pulse. In some embodiments, because front-end 400/420 is pulsed to save power, the photocurrent in photodiode 203 is generated for short intervals when LED 202 is on and drops to zero (plus some small ambient contribution) for a majority of the time (when LED 202 is off).

The pulsed operation may cause the TIA feedback current through resistor Rf to drop, sometimes considerably if the DC component is large. In some embodiments, V-to-I Converter 421 looks at what the DC photodiode current was in the last LED on phase by taking the difference in Iref*Rf and the voltage held on the capacitor of S/H LP Filter 302 and translating the difference into a current sink which is activated during all of or part of the interval where LED 202 is off. As such, in some embodiments, TIA 303 re-establishes or maintains its correct output level and does not suffer discontinuities as LED 202 is turned on and off. One technical effect of V-to-I Converter 421 is that the overall power consumption of Block 204 of FIG. 2 reduces and the circuit design upstream can be made more straightforward.

Referring back to FIG. 4B, in some embodiments, during the off period of LED 202, V-to-I Converter 421 is activated (because of Phi_b is high, which is an inverse of Phi). In this example, Phi is low to turn off LED 202 and high to turn on LED 202. However, the logic can be inversed to achieve the same effect without changing the essence of various embodiments. In one such embodiment, the DC voltage on the filter capacitor of S/H LP Filter 302 is converted to DC offset current component (Ia) present at the inverting input of TIA 303 when LED 202 was on. Here, "Ia" is a current flowing into the top terminal of V-to-I Converter 421. Current "Ia" mimics the photodiode current which no longer flows when the LED 202 is off.

In some embodiments, the current from photodiode 203 in the LED off phase is also compensated for by V-to-I Converter 421. This is done by seeing that "Vref" is Iref*Rf and then comparing this voltage to the actual correction voltage held on the non-inverting input (on the sample and hold capacitor), in accordance with some embodiments. The difference in these two voltages divided by Rf gives the DC current the circuit was correcting for in the last LED on phase. As such, this current can be generated and pulled through the TIA feedback resistor Rf keeping its output continuous between the LED on and off phases.

As such, the output Vout of TIA 303 is maintained at the correct DC level throughout the phase cycle ready to pick up the AC component again when LED 202 is turned back on again. This lowers the bandwidth and slewing requirements in TIA 303. In some embodiments, because of V-to-I Converter 421, TIA 303 may not need to slew quickly to convey the fast pulses of information. As such, TIA 303 could be made incapable of passing the so called "motion artifacts" which can manifest as large unwanted pulses in photodiode current as the user of the PPG device (e.g., a smartwatch) moves about, in accordance with some embodiments.

Figure 5:
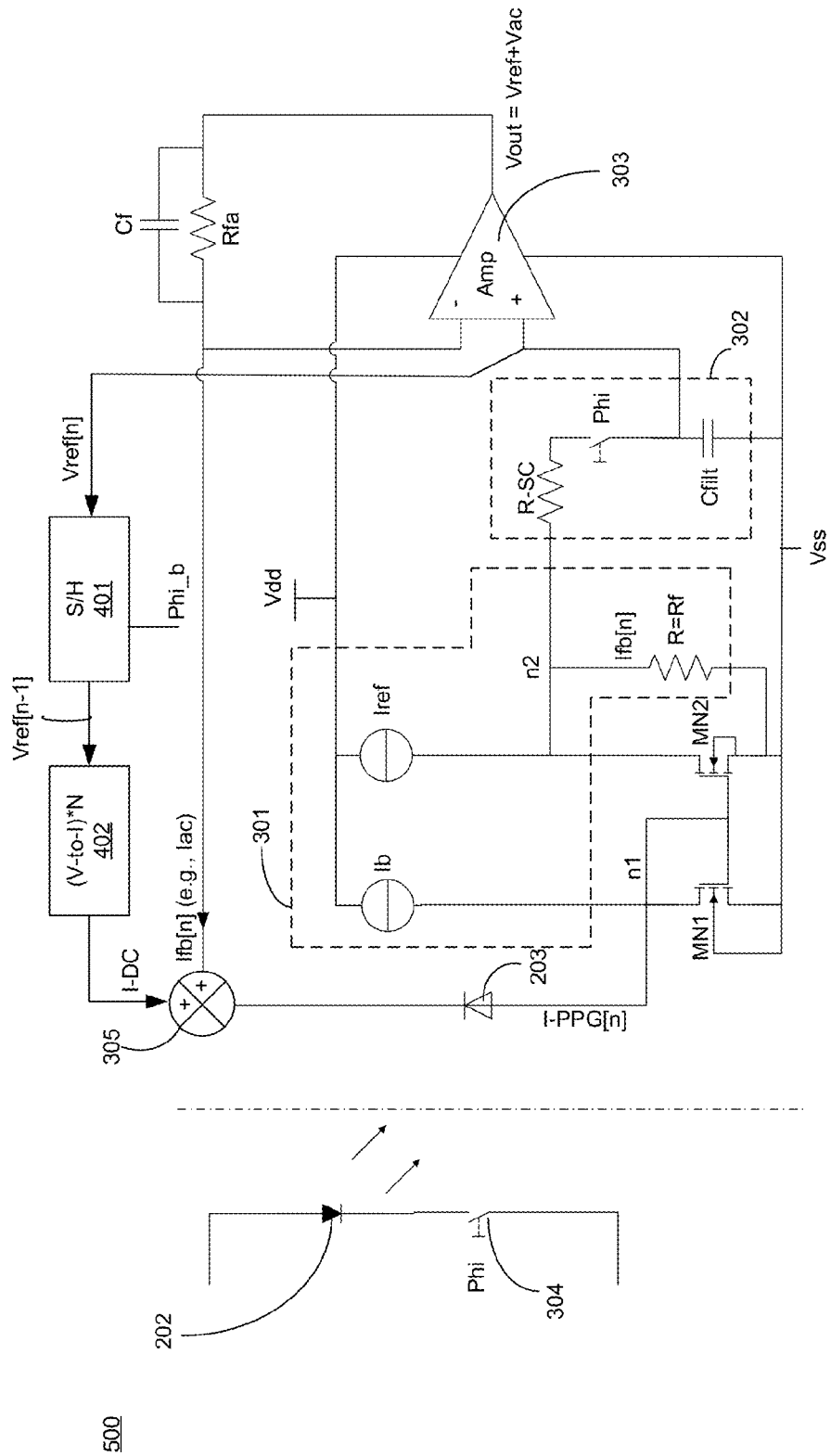
FIG. 5 illustrates an apparatus showing a transistor-level linear feedforward path coupled to the non-inverting input of the amplifier, and a sampled feedback loop, according to some embodiments of the disclosure.

FIG. 5 illustrates apparatus 500 with a transistor-level linear feedforward path coupled to the non-inverting input of the amplifier, and a sampled feedback loop, according to some embodiments of the disclosure. It is pointed out that those elements of FIG. 5 having the same reference numbers (or names) as the elements of any other figure can operate or function in any manner similar to that described, but are not limited to such.

In some embodiments, I-to-V Converter 301 comprises a bias current source Ib, reference current source Iref, and replica resistor Rf coupled together as shown. In some embodiments, the bias current source Ib provides bias current Ib to transistor MN1. In some embodiments, S/H LP Filter 302 comprises switching resistor and capacitor R-SC (e.g., MOS resistor) and Cfilt (e.g., a MOS capacitor), respectively, coupled together via a switch controlled by Phi.

In some embodiments, the photocurrent mirrored through transistors MN1 and MN2 is subtracted from Iref and then dropped into resistor Rf (having the same resistance as the resistance of the feedback resistor Rf coupled to TIA 303). This gives a voltage of maximum value Iref*Rf, which drops as the photocurrent rises, in accordance with some embodiments. In some embodiments, the voltage on node n2 can be filtered with a low frequency pole to remove all or most components of AC signal leaving flicker noise and DC components. The voltage stored on capacitor Cfilt is then presented to the non-inverting TIA input, in accordance with some embodiments.

The effect is akin to a static Vref on the non-inverting input (of TIA 303) dropping in sympathy with increasing photodiode DC current (e.g., because Vref is scaled by resistance Rf, Vref drops by the exact amount Vout would have risen by to push the DC component back through the feedback resistor Rf). By presenting this filtered DC voltage to the non-inverting input of TIA 303, the output of TIA 303 is driven downwards by the exact amount it would have risen upwards to provide the DC offset current. As such, in some embodiments, the output voltage of TIA 303 is notionally free of the DC photodiode current but facilitates a gain of Rf exclusively to the AC photocurrent. The large DC voltage excursion that would have appeared at the output of TIA 303 now appears as a negative excursion from the reference level (i.e., (Iref$-I_{DC}$)·Rf) at the non-inverting input of TIA 303, in accordance with some embodiments.

Figure 6:
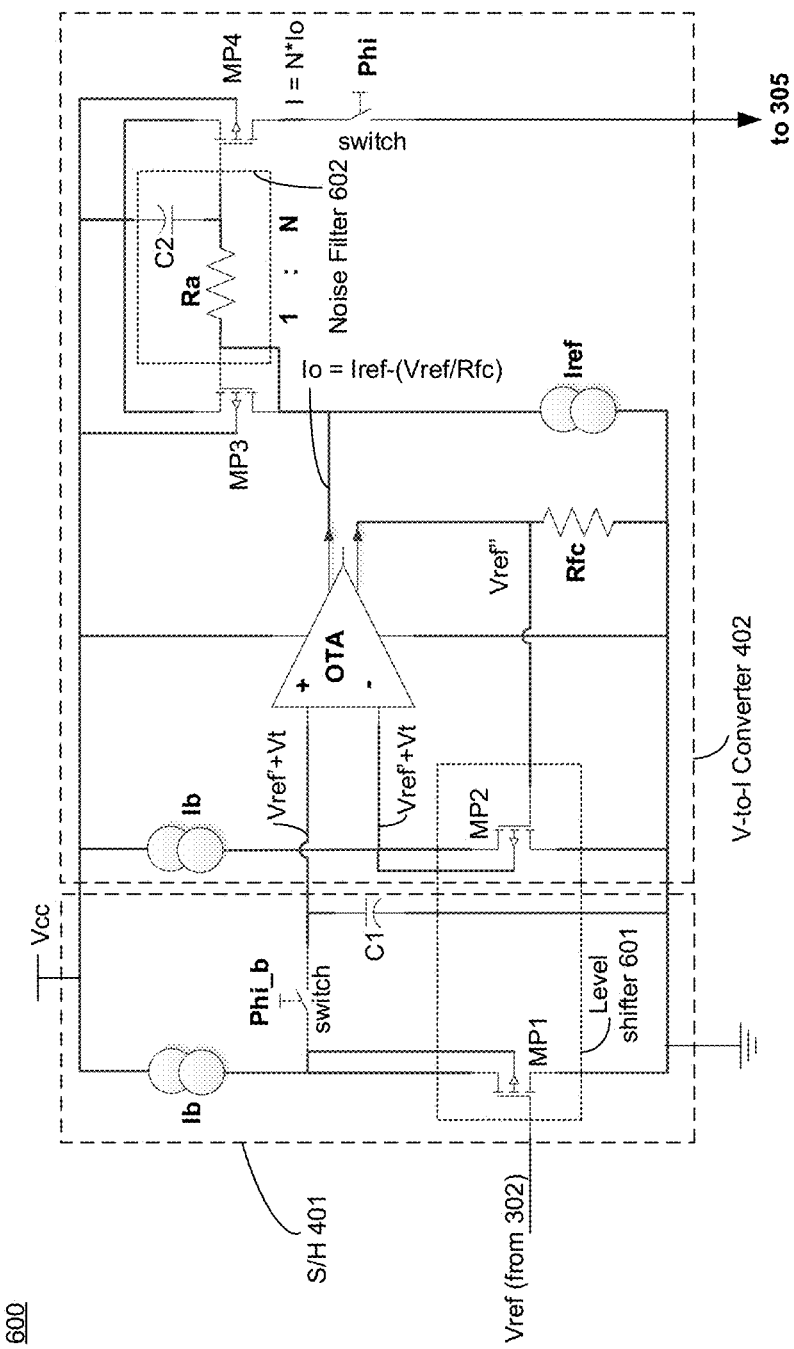
FIG. 6 illustrates an apparatus showing a transistor-level sampled feedback loop, according to some embodiments of the disclosure.

FIG. 6 illustrates apparatus 600 showing a transistor-level sampled feedback loop, according to some embodiments of the disclosure. It is pointed out that those elements of FIG. 6 having the same reference numbers (or names) as the elements of any other figure can operate or function in any manner similar to that described, but are not limited to such. A person skilled in the art would appreciate that the concepts of the various embodiments can have various implementations that draw inspiration from apparatus 600, and are considered part of this description.

In some embodiments, S/H circuit 401 of the second feedback loop includes a switch controllably by Phi_b and a storage device (e.g., capacitor C1). The switch can be implemented using any known schemes. For example, the switch is transistor pass-gate with a gate terminal coupled to Phi_b. In some embodiments, the second feedback loop includes a level shifter 601 integrated within S/H circuit 401. In some embodiments, level shifter 601 comprises p-type transistors MP1 and MP2 coupled together as shown. In some embodiments, a current source Ib is coupled to the switch and transistor MP1. In some embodiments, the output Vref of S/H LP 302 is received by the gate terminal of transistor MP1. This output is then sampled by the switch when Phi_b is high, and provided as Vref+Vt to V-to-I Converter 402.

In some embodiments, V-to-I Converter 402 comprises a dual output and dual input operational transconductance amplifier (OTA). OTA is an amplifier whose differential input voltage produces an output current. In some embodiments, the non-inverting input of the OTA is coupled to the storage device of S/H Circuit 401. As such, Vref+Vt is received by the non-inverting input of the OTA. In some embodiments, the added "+Vt" (level shift) allows easier current mirror design and implementation. In some embodiments, the inverting input of the OTA is coupled to transistor MP2, and also receives Vref+Vt. In some embodiments, the first output of the OTA provides current to resistor Rfc. The voltage Vref" across resistor Rfc biases the gate terminal of transistor MP2.

In some embodiments, the second output of the OTA provides current to Noise Filter 602 via current mirror formed by p-type transistors MP3 and MP4. In some embodiments, the output current from the second output of the OTA is Io−Iref−(Vref/Rfc), where Iref is a current source coupled MP3 (which is diode connected). In some embodiments, current Io is multiplied by 'N' (where 'N' is an integer, and is the ratio of the sizes of transistors MP3 and MP4). A person skilled in the art would appreciate that the current mirror can be formed from BJT instead of MOSFET to achieve lower in-band noise. As such, V-to-I Converter 402 has a configurable current gain. In some embodiments, the multiplied current I=N*Io is sampled by another switch which operates using Phi and summed at summing node 305. In some embodiments, Noise Filter 602 is a low pass filter implemented with resistor Ra and capacitor C2. In some embodiments, Noise Filter 602 is coupled to the gate terminals of MP3 and MP4. While the resistors and capacitors of various embodiments are show as passive devices, they can be implemented using various technologies (e.g., transistor based capacitor and resistor, metal capacitor, hybrid of metal capacitor and transistor capacitor, etc.).

FIG. 7 illustrates apparatus 700 with a transistor-level feedforward path coupled to the non-inverting input of the amplifier, and a sampled feedback loop, according to some embodiments of the disclosure. It is pointed out that those elements of FIG. 7 having the same reference numbers (or names) as the elements of any other figure can operate or function in any manner similar to that described, but are not limited to such. So as not to obscure the embodiments, differences between FIG. 7 and FIG. 5 are described.

In some embodiments, instead of node n2 coupling directly to S/H LP Filter 302, node n2 is coupled to a gate terminal of a p-type transistor MP1. In some embodiments, the p-type transistor MP1 is coupled in series with a current source Ib. This current source may not have to relate to Ib in transistor MN1. In some embodiments, the value of current Ib is determined by noise requirements, slewing on node n3, and other design parameters which may become relevant in an implementation. Because resistor R-SC may be such high impedance to get a low frequency pole, the current in Ib may not affect the RC filter too much in operation, in accordance with some embodiments.

In some embodiments, the resistor R-SC of S/H LP Filter 302 is coupled to the source terminal of transistor MP1. In some embodiments, the output voltage on node n2 of I-to-V Converter 301 is level shifted up and buffered by the transistor MP1. Such level shifting can be beneficial if the DC offset overloads I-to-V Converter 301 and sends or collapses V1 to ground (i.e., V1 clips). For example, transistor MP1 can ensure the voltage levels of the terminals or nodes of amplifier 303 do not drop below a $V_{threshold}$ and therefore the voltage across photodiode 203 stays at a $V_{threshold}$ keeping photodiode 203 reverse biased. In some embodiments, transistor MP1 also buffers the output of I-to-V Converter 301 before meeting with RC sample and hold filter 302. In some embodiments, the buffered voltage on node n3 is filtered with a large time constant using the on-die capacitor Cfilt and resistor R-SC and fed forward to the non-inverting input of TIA 303. In some embodiments, the on-die capacitor Cfilt and the resistor R-SC are part of S/H LP Filter 302.

Figure 8:
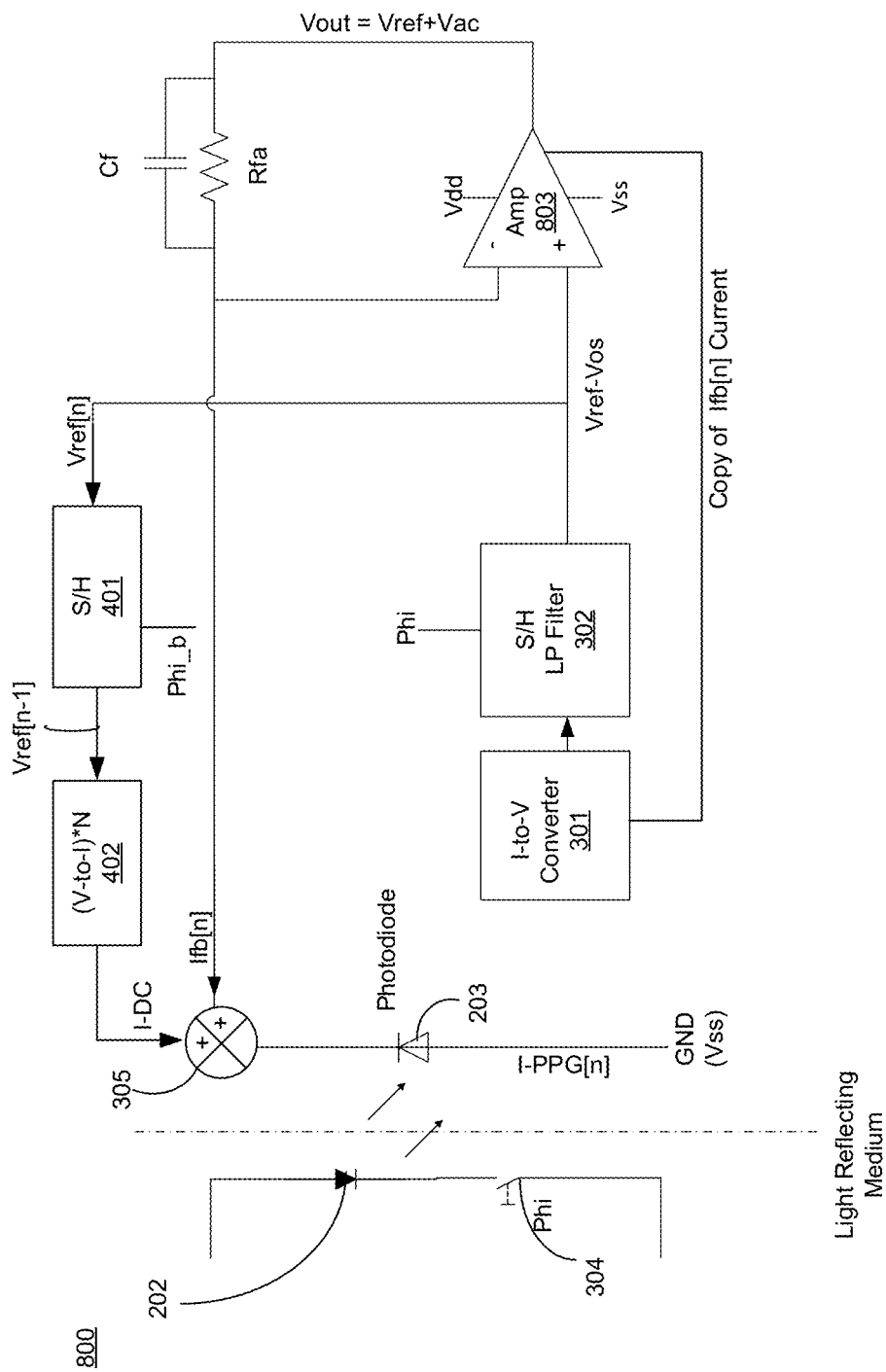
FIG. 8 illustrates an apparatus showing a linear feedforward path coupled to the non-inverting input of the amplifier, where the feedforward path uses a copy of the photodiode current, and a sampled feedback loop, according to some embodiments of the disclosure.

FIG. 8 illustrates apparatus 800 including a linear feedforward path coupled to the non-inverting input of the amplifier, where the feedforward path uses a copy of the photodiode current, and a sampled feedback loop, according to some embodiments of the disclosure. It is pointed out that those elements of FIG. 8 having the same reference numbers (or names) as the elements of any other figure can operate or function in any manner similar to that described, but are not limited to such. So as not to obscure the embodiments of FIG. 8, differences between FIG. 3 and FIG. 8 are described. Functionally, apparatus 800 is equivalent to apparatus 300, but different in implementation.

In some embodiments, instead of mirroring the current of photodiode 203, a copy of the photodiode current is used by I-to-V Converter 301. In one such embodiment, the anode of photodiode 203 is coupled to ground (i.e., Vss). In some embodiments, amplifier 303 is replaced with a dual output amplifier 803. In some embodiments, a first output of amplifier 803 provides a copy of photodiode current as a copy of I-Rfa (same as ifb[n]) current to I-to-V Converter 301. In some embodiments, the second output of amplifier 803 is a voltage Vout. In some embodiments, the second output of amplifier 803 is current Ifb[n] which results in voltage Vout at one terminal of resistor Rfa. The voltage Vout depends on the current times Rfa (giving useful transimpedance gain) while the current Ifb[n] is the current supplied back to photodiode 203. As such, by copying the output stage, the current that would have flowed back through resistor Rfa to Photodiode 203 is duplicated and instead diverted into a current mirror which drives I-to-V Converter 301.

Figure 9:
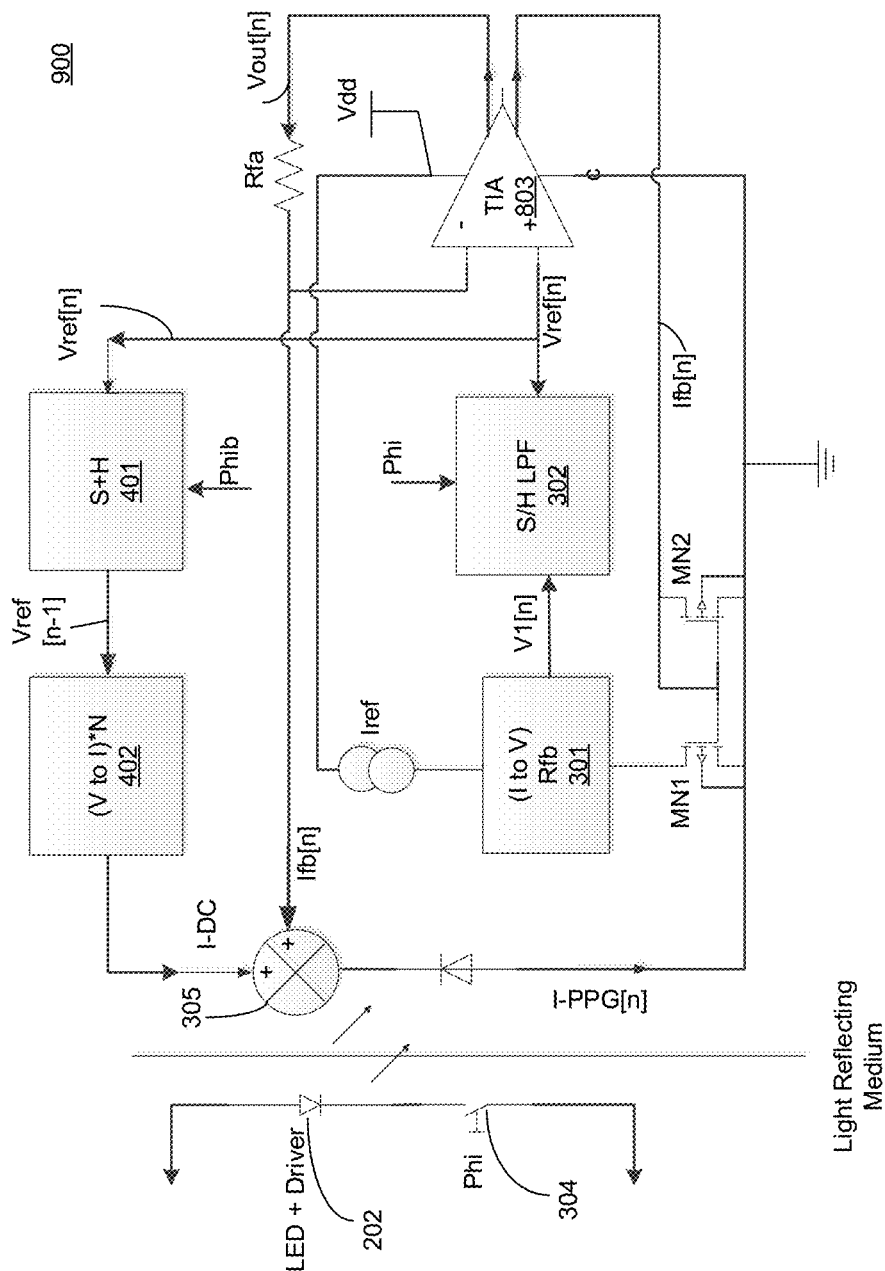
FIG. 9 illustrates an apparatus showing a linear feedforward path coupled to the non-inverting input of the amplifier, where the feedforward path uses a copy of the photodiode current, and a sampled feedback loop, according to some embodiments of the disclosure.

FIG. 9 illustrates apparatus 900 including a linear feedforward path coupled to the non-inverting input of the amplifier, where the feedforward path uses a copy of the photodiode current, and a sampled feedback loop, according to some embodiments of the disclosure. It is pointed out that those elements of FIG. 9 having the same reference numbers (or names) as the elements of any other figure can operate or function in any manner similar to that described, but are not limited to such.

So as not to obscure the embodiments of FIG. 9, differences between FIG. 4 and FIG. 9 are described. Functionally, apparatus 900 is equivalent to apparatus 400, but different in implementation. In some embodiments, instead of mirroring the current of photodiode 203, a copy of the photodiode current is used by I-to-V Converter 301. In one such embodiment, the anode of photodiode 203 is coupled to ground (i.e., Vss). In some embodiments, instead of using a single output amplifier 303, a dual output amplifier 803 is used that provides current Ifb[n] which is copied over by transistors MN2 and MN1 to I-to-V Converter 302. For example, the output of TIA 803 provides a copy of photodiode current as a copy of I-Rfa current (same as Ifb[n]) to I-to-V Converter 301. One technical effect of using the copy of I-RFa is that a package pin can be saved because merely an access tone terminal of photodiode 203 is needed (e.g., there may not be a need to bias a series MOSFET that forms the in-line current mirror).

Figure 10:
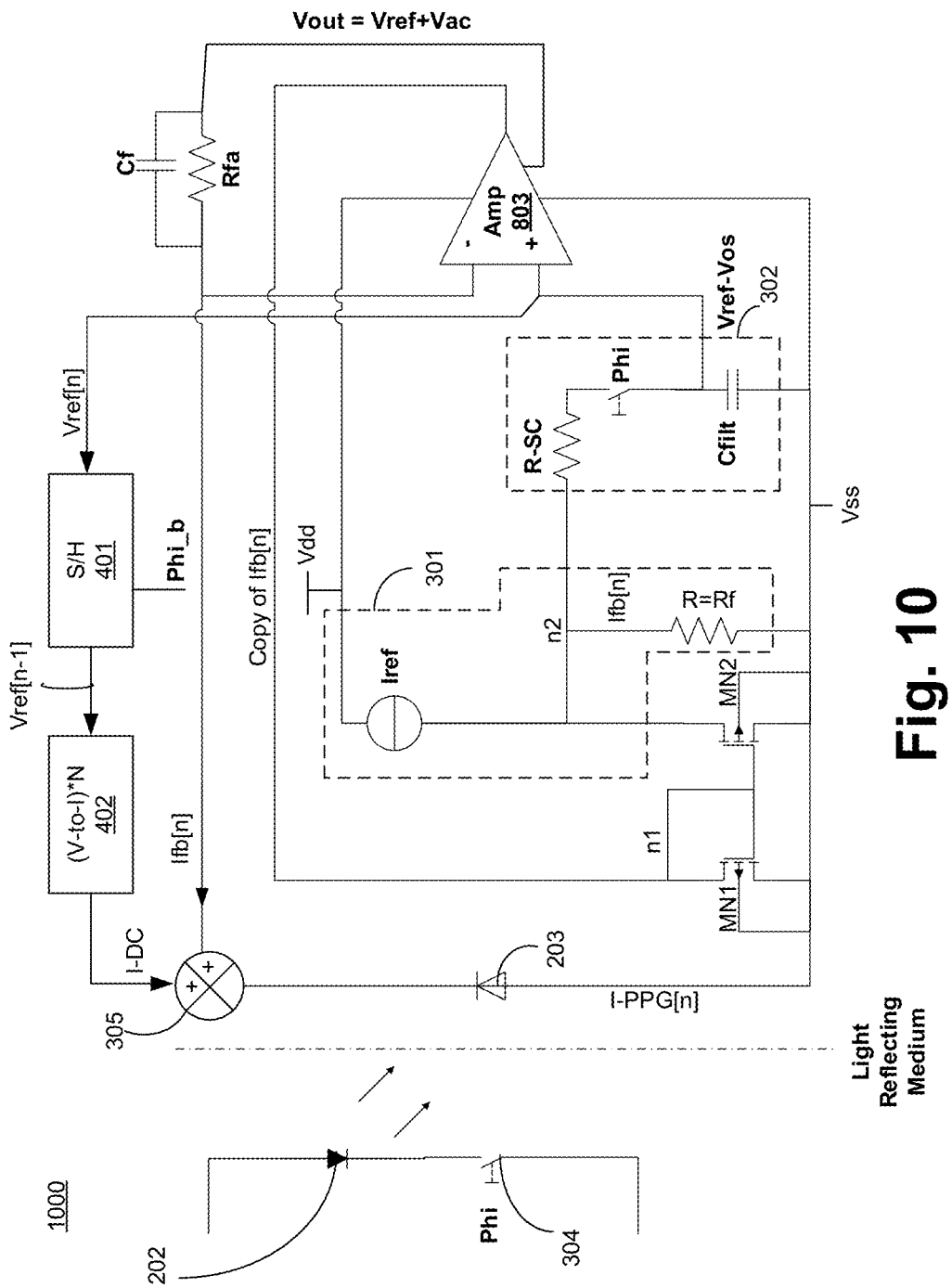
FIG. 10 illustrates an apparatus showing a transistor-level linear feedforward path, where the feedforward path uses a copy of the photodiode current, and a sampled feedback loop, according to some embodiments of the disclosure.

FIG. 10 illustrates apparatus 1000 with a transistor-level linear feedforward path, where the feedforward path uses a copy of the photodiode current, and a sampled feedback loop, according to some embodiments of the disclosure. It is pointed out that those elements of FIG. 10 having the same reference numbers (or names) as the elements of any other figure can operate or function in any manner similar to that described, but are not limited to such. So as not to obscure the embodiments of FIG. 10, differences between FIG. 10 and FIG. 5 are described. Functionally, transistor-level feed-forward path 1000 is similar to transistor-level feedforward path 500.

In some embodiments, instead of transistor MN1 receiving current (Ifb) directly from photodiode 203, a copy of the photodiode current (i.e., copy of Ifb) is used to bias transistor MN1. In some embodiments, this current is mirrored from transistor MN1 to transistor MN2 and then converted to voltage on node n2. Node n2 is coupled to resistor R-SC.

While the various embodiments are described with reference to n-type current mirror for mirroring the current of photodiode 203, or for mirroring a copy of the current, the circuit implementations of various embodiments can be re-configured using p-type devices instead. In other examples, the current mirror and other circuits can be synthesized with BJT, MOS trans-linear, current mode, log domain, route domain circuits. This notion applies to the various embodiments (e.g., the choice of transistor type can be changed and the design can be modified accordingly without changing the essence of the embodiments). All such modifications are considered within the scope of the various embodiments.

Figure 11:
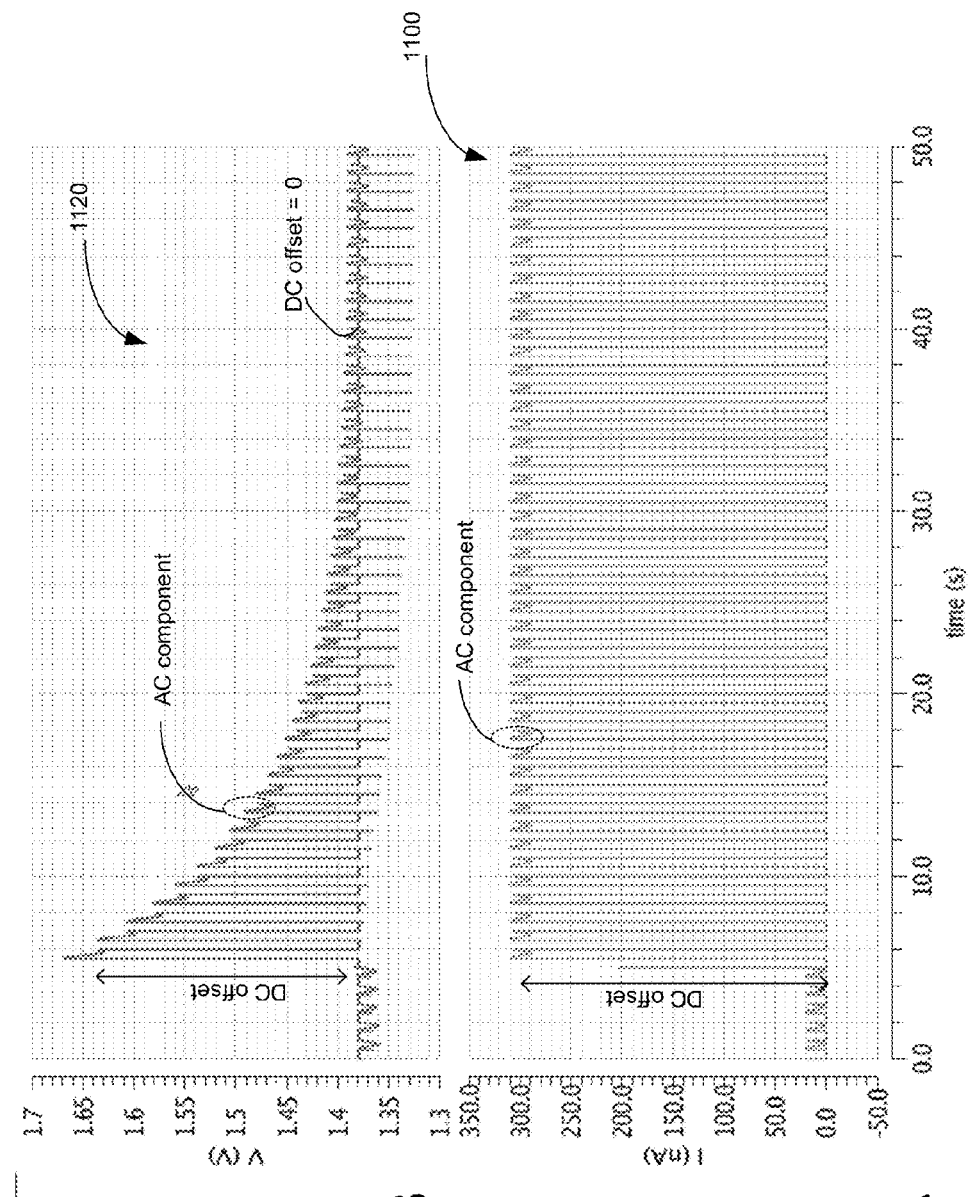
FIGS. 11A-B illustrate plots showing input current AC and DC components and cancelling of DC offset using the apparatus of various embodiments.

FIGS. 11A-B illustrate plots 1100 and 1120 showing input current AC and DC components and cancelling of DC offset using the apparatus of various embodiments. It is pointed out that those elements of FIGS. 11A-B having the same reference numbers (or names) as the elements of any other figure can operate or function in any manner similar to that described, but are not limited to such.

For plot FIG. 11A, x-axis is time in seconds and y-axis is current in nano Amperes (nA). In this example, from time 0 to about 5 seconds, there is no DC offset in the photodiode current to illustrate the ideal situation. The waveform of plot 1100 shows the DC component of the photodiode current (i.e., DC Offset) and the AC component of the photodiode current. The AC component is the signal of interest which resides on top of the DC component.

For plot FIG. 11B, x-axis is time in seconds and y-axis is voltage in Volts. In this example, from time 0 to about 5 seconds, there is no DC offset in the output of TIA 303 to illustrate the ideal situation. The waveform of plot 1120 shows the DC component (i.e., DC Offset) at the output of TIA 303 and the corresponding AC component. The apparatus of various embodiments slowly cancels the DC offset from the output voltage of TIA 303, and after about 30 seconds, the DC offset is substantially removed. The AC component is the signal of interest, and which is left over for further processing.

Figure 12:
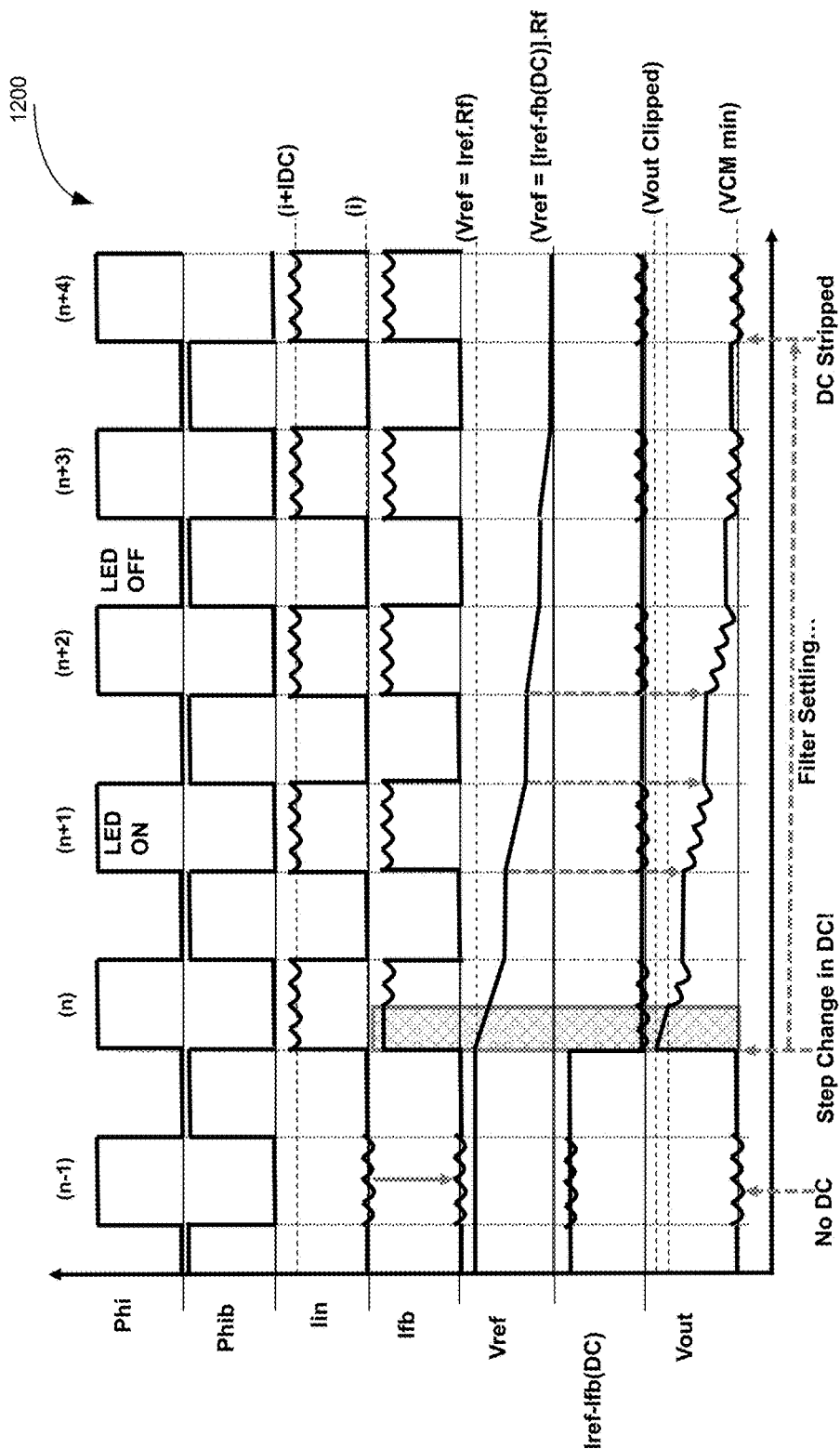
FIG. 12 illustrate a timing diagram showing cancelling of DC offset using the single loop apparatus of FIG. 3.

FIG. 12 illustrate timing diagram 1200 showing cancelling of DC offset using the apparatus of FIG. 3. It is pointed out that those elements of FIG. 12 having the same reference numbers (or names) as the elements of any other figure can operate or function in any manner similar to that described, but are not limited to such. Here, x-axis is time and y-axis is voltage, logic level, or current. The waveforms from the top are clocks Phi and Phi_b (same as Phib), input current Iin (which is same as I-PPG[n]), feedback current Ifb (same as I-Rfa or I-Rf), reference voltage Vref (which is output of S/H LP 302), difference of current Iref and Ifb, and output Vout. Timing diagram shows how DC component or DC offset is removed from Vout while the AC signal (which in this example is the signal of interest) is preserved.

Timing diagram 1200 is a similar case to that of FIGS. 11A-B. Here, a DC step in Iin is seen and various nodes of the single feedback loop circuit are plotted. Initially Ifb clips due to the offset magnitude but it recovers as Vref drops. Vref is a filtered version of (Iref−Ifb)/Rfb which can be seen to dive straight to the required DC offset level it would also contain signal information as it is unfiltered. Note, Iref−Ifb may stay at the correct level throughout from now on in order to drive the filter to the correct level. It is therefore possible to keep S/H LP 302 connected to the output of the IV stage during both Phi and Phib to get an improved settling time. i.e. because the current is maintained in the output stage of the Amplifier 303 via Rf during LED off periods the I-to-V Converter 301 will still be outputting the correct target voltage for S/H LP 302. So leaving the filter in the sample phase would allow it more time to settle between pulses and speed up the acquisition of the system. It may ensure the DC component which flows back through Rf during Phi is maintained during Phib to prevent the output slewing too much. Eventually the Vout voltage returns to its original quiescent level once the filter is settled.

Figure 13:
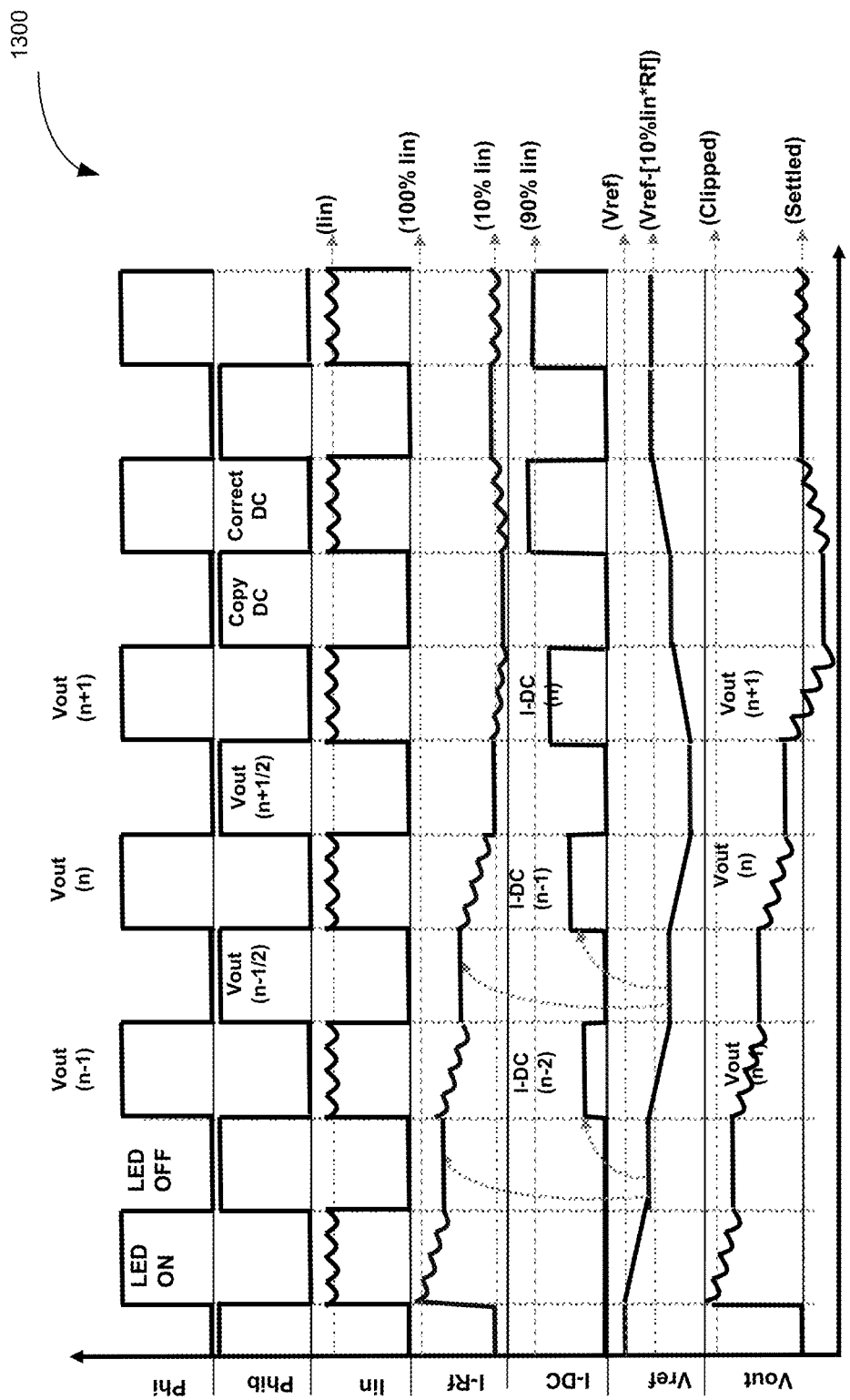
FIG. 13 illustrate a timing diagram showing cancelling of DC offset using the dual loop apparatus of various embodiments.

FIG. 13 illustrate a timing diagram 1300 showing cancelling of DC offset using the apparatus of various embodiments. It is pointed out that those elements of FIG. 13 having the same reference numbers (or names) as the elements of any other figure can operate or function in any manner similar to that described, but are not limited to such.

Here, x-axis is time and y-axis is voltage, logic level, or current. The waveforms from the top are clocks Phi and Phi_b (same as Phib), input current Iin (which is same as I-PPG[n]), feedback current Ifb (same as I-Rfa or I-Rf), current I-DC provided by the second feedback loop, reference voltage Vref (which is output of S/F LP 302), and output Vout. Like timing diagram 1300, here DC offset is removed and AC signal is preserved (See output Vout). Unlike Vref of timing diagram 1200, here Vref is high enough to allow increasing the size of Rfa which improves the DC offset cancelling tolerance.

FIG. 13 is much the same as FIG. 12 although now there is another current waveform to observe, I-DC. It can be seen that I-DC flows when Phi is '1' with a magnitude which corresponds to the DC offset component that was present in Vref after the previous Phi='1' phase. FIG. 13 shows two feedback elements working together to feed the DC current I-DC back into photodiode 203 there will come a point where both the loops settle. Depending on the gain of the second loop, the cut-off frequency of low pass filter 302 and the pulse frequency there may be a degree of ringing in settling the system which is indicated with a small over shoot in Vout. Note how this time Vref largely recovers its range once the second loop has settled in. This example shows a case where merely 10% of I-DC ends up flowing back through Rf.

Figure 14:
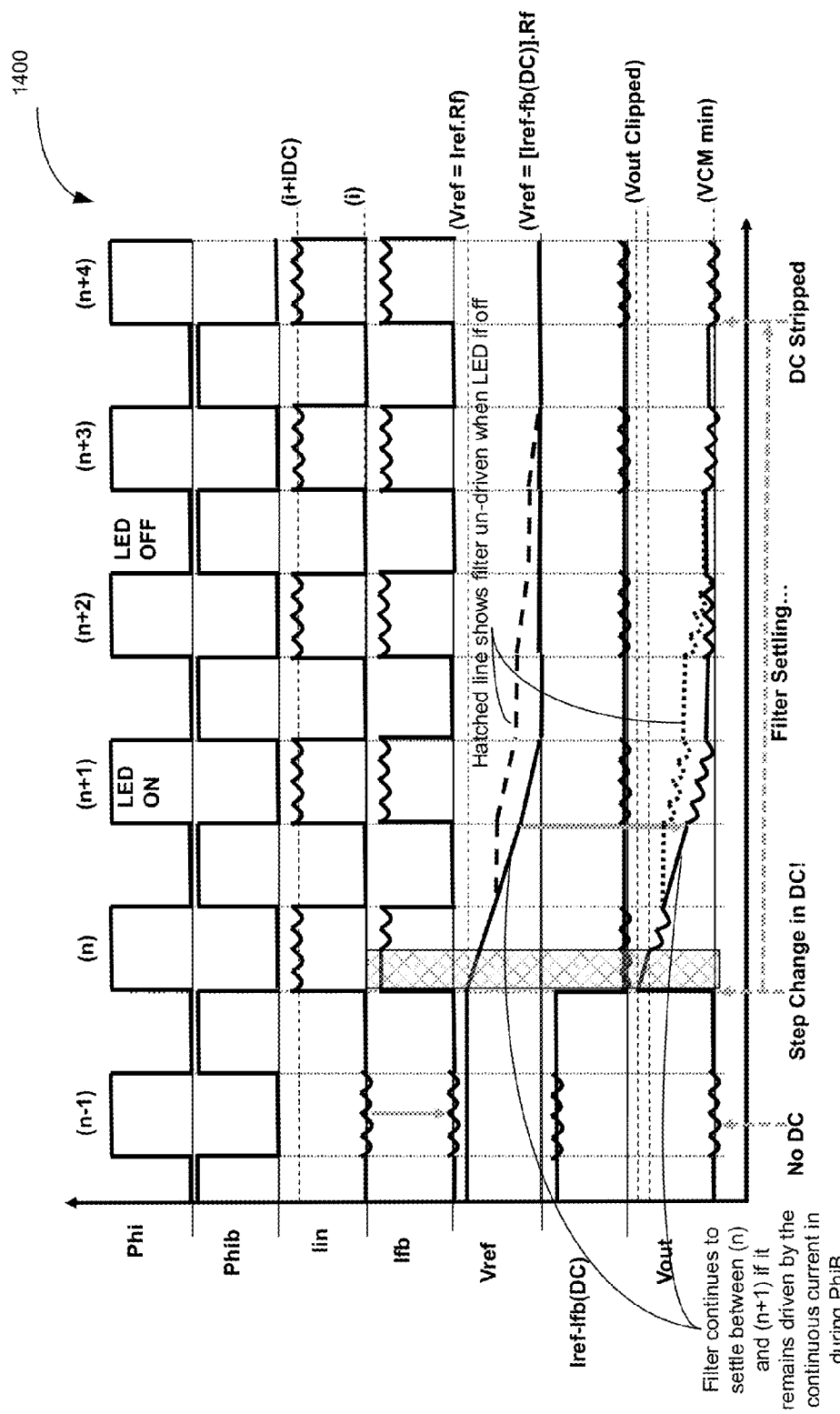
FIG. 14 illustrate a timing diagram showing cancelling of DC offset using the dual loop and/or signal loop apparatus of various embodiments.

FIG. 14 illustrate timing diagram 1400 showing cancelling of DC offset using the dual loop and/or signal loop apparatus of various embodiments. It is pointed out that those elements of FIG. 14 having the same reference numbers (or names) as the elements of any other figure can operate or function in any manner similar to that described, but are not limited to such.

Here, x-axis is time and y-axis is voltage, logic level, or current. Timing diagram 1400 is similar to timing diagram 1300 except that more improved settling time is achieved in accordance with some embodiments. Note, Iref−Ifb may stay at the correct level throughout from now on in order to drive the filter to the correct level. It is therefore possible (e.g., optional) to keep the S/H LP 302 connected to the output of the IV stage during both Phi and Phib to get an improved settling time. For example, because the current is maintained in the output stage of the Amplifier 303 via Rf during LED off periods the I-to-V Converter 301 may still be outputting the correct target voltage for S/H LP 302. So leaving S/H LP 302 in the sample phase may allow it more time to settle between pulses and speed up the acquisition of the system, in accordance with some embodiment.

Figure 15:
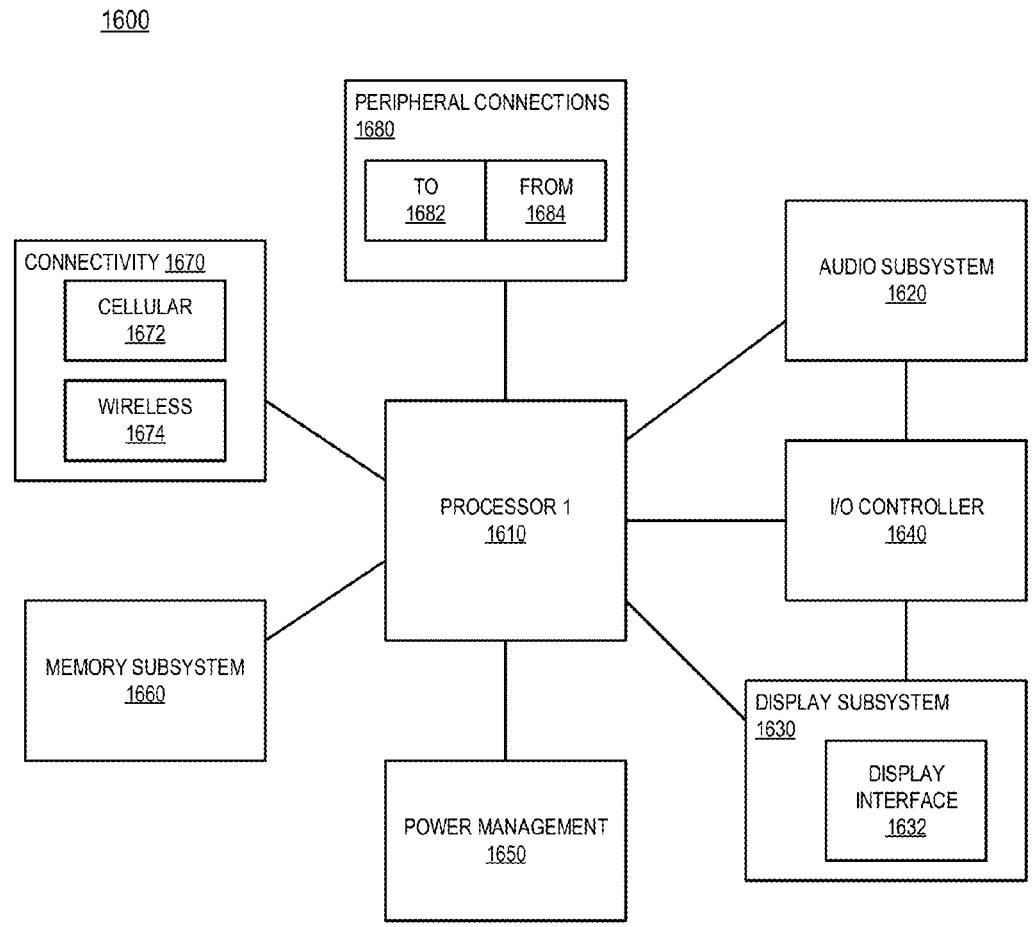
FIG. 15 illustrates a smart device or a computer system or a SoC with apparatus to cancel DC offset, according to some embodiments.

FIG. 15 illustrates a smart device or a computer system or a SoC 1600 with apparatus to cancel DC offset, according to some embodiments. It is pointed out that those elements of FIG. 15 having the same reference numbers (or names) as the elements of any other figure can operate or function in any manner similar to that described, but are not limited to such. While the embodiments are described with reference to detecting PPG signals, the DC offset cancelling techniques of various embodiments can be used in any circuit of computer system 1600.

FIG. 15 illustrates a block diagram of an embodiment of a mobile device in which flat surface interface connectors could be used. In some embodiments, computing device 1600 represents a mobile computing device, such as a computing tablet, a mobile phone or smart-phone, a wireless-enabled e-reader, or other wireless mobile device. It will be understood that certain components are shown generally, and not all components of such a device are shown in computing device 1600.

In some embodiments, computing device 1600 includes a first processor 1610 with apparatus to track and cancel DC offset, according to some embodiments discussed. Other blocks of the computing device 1600 may also include the apparatus to track and cancel DC offset, according to some embodiments. The various embodiments of the present disclosure may also comprise a network interface within 1670 such as a wireless interface so that a system embodiment may be incorporated into a wireless device, for example, cell phone or personal digital assistant.

In one embodiment, processor 1610 (and/or processor 1690) can include one or more physical devices, such as microprocessors, application processors, microcontrollers, programmable logic devices, or other processing means. The processing operations performed by processor 1610 include the execution of an operating platform or operating system on which applications and/or device functions are executed. The processing operations include operations related to I/O (input/output) with a human user or with other devices, operations related to power management, and/or operations related to connecting the computing device 1600 to another device. The processing operations may also include operations related to audio I/O and/or display I/O.

In one embodiment, computing device 1600 includes audio subsystem 1620, which represents hardware (e.g., audio hardware and audio circuits) and software (e.g., drivers, codecs) components associated with providing audio functions to the computing device. Audio functions can include speaker and/or headphone output, as well as microphone input. In some embodiments, audio subsystem 1620 includes apparatus and/or machine executable instructions to avoid self-hearing, according to some embodiments. Devices for such functions can be integrated into computing device 1600, or connected to the computing device 1600. In one embodiment, a user interacts with the computing device 1600 by providing audio commands that are received and processed by processor 1610.

Display subsystem 1630 represents hardware (e.g., display devices) and software (e.g., drivers) components that provide a visual and/or tactile display for a user to interact with the computing device 1600. Display subsystem 1630 includes display interface 1632, which includes the particular screen or hardware device used to provide a display to a user. In one embodiment, display interface 1632 includes logic separate from processor 1610 to perform at least some processing related to the display. In one embodiment, display subsystem 1630 includes a touch screen (or touch pad) device that provides both output and input to a user.

I/O controller 1640 represents hardware devices and software components related to interaction with a user. I/O controller 1640 is operable to manage hardware that is part of audio subsystem 1620 and/or display subsystem 1630. Additionally, I/O controller 1640 illustrates a connection point for additional devices that connect to computing device 1600 through which a user might interact with the system. For example, devices that can be attached to the computing device 1600 might include microphone devices, speaker or stereo systems, video systems or other display devices, keyboard or keypad devices, or other I/O devices for use with specific applications such as card readers or other devices.

As mentioned above, I/O controller 1640 can interact with audio subsystem 1620 and/or display subsystem 1630. For example, input through a microphone or other audio device can provide input or commands for one or more applications or functions of the computing device 1600. Additionally, audio output can be provided instead of, or in addition to display output. In another example, if display subsystem 1630 includes a touch screen, the display device also acts as an input device, which can be at least partially managed by I/O controller 1640. There can also be additional buttons or switches on the computing device 1600 to provide I/O functions managed by I/O controller 1640.

In one embodiment, I/O controller 1640 manages devices such as accelerometers, cameras, light sensors or other environmental sensors, or other hardware that can be included in the computing device 1600. The input can be part of direct user interaction, as well as providing environmental input to the system to influence its operations (such as filtering for noise, adjusting displays for brightness detection, applying a flash for a camera, or other features).

In one embodiment, computing device 1600 includes power management 1650 that manages battery power usage, charging of the battery, and features related to power saving operation. Memory subsystem 1660 includes memory devices for storing information in computing device 1600. Memory can include nonvolatile (state does not change if power to the memory device is interrupted) and/or volatile (state is indeterminate if power to the memory device is interrupted) memory devices. Memory subsystem 1660 can store application data, user data, music, photos, documents, or other data, as well as system data (whether long-term or temporary) related to the execution of the applications and functions of the computing device 1600.

Elements of embodiments are also provided as a machine-readable medium (e.g., memory 1660) for storing the computer-executable instructions (e.g., instructions to implement any other processes discussed herein). The machine-readable medium (e.g., memory 1660) may include, but is not limited to, flash memory, optical disks, CD-ROMs, DVD ROMs, RAMs, EPROMs, EEPROMs, magnetic or optical cards, phase change memory (PCM), or other types of machine-readable media suitable for storing electronic or computer-executable instructions. For example, embodiments of the disclosure may be downloaded as a computer program (e.g., BIOS) which may be transferred from a remote computer (e.g., a server) to a requesting computer (e.g., a client) by way of data signals via a communication link (e.g., a modem or network connection).

Connectivity 1670 includes hardware devices (e.g., wireless and/or wired connectors and communication hardware) and software components (e.g., drivers, protocol stacks) to enable the computing device 1600 to communicate with external devices. The computing device 1600 could be separate devices, such as other computing devices, wireless access points or base stations, as well as peripherals such as headsets, printers, or other devices.

Connectivity 1670 can include multiple different types of connectivity. To generalize, the computing device 1600 is illustrated with cellular connectivity 1672 and wireless connectivity 1674. Cellular connectivity 1672 refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, or other cellular service standards. Wireless connectivity (or wireless interface) 1674 refers to wireless connectivity that is not cellular, and can include personal area networks (such as Bluetooth, Near Field, etc.), local area networks (such as Wi-Fi), and/or wide area networks (such as WiMax), or other wireless communication.

Peripheral connections 1680 include hardware interfaces and connectors, as well as software components (e.g., drivers, protocol stacks) to make peripheral connections. It will be understood that the computing device 1600 could be a peripheral device ("to" 1682) to other computing devices, as well as have peripheral devices ("from" 1684) connected to it. The computing device 1600 commonly has a "docking" connector to connect to other computing devices for purposes such as managing (e.g., downloading and/or uploading, changing, synchronizing) content on computing device 1600. Additionally, a docking connector can allow computing device 1600 to connect to certain peripherals that allow the computing device 1600 to control content output, for example, to audiovisual or other systems.

In addition to a proprietary docking connector or other proprietary connection hardware, the computing device 1600 can make peripheral connections 1680 via common or standards-based connectors. Common types can include a Universal Serial Bus (USB) connector (which can include any of a number of different hardware interfaces), DisplayPort including MiniDisplayPort (MDP), High Definition Multimedia Interface (HDMI), Firewire, or other types.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the elements. If the specification or claims refer to "an additional" element, that does not preclude there being more than one of the additional element.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

While the disclosure has been described in conjunction with specific embodiments thereof, many alternatives, modifications and variations of such embodiments will be apparent to those of ordinary skill in the art in light of the foregoing description. For example, other memory architectures e.g., Dynamic RAM (DRAM) may use the embodiments discussed. The embodiments of the disclosure are intended to embrace all such alternatives, modifications, and variations as to fall within the broad scope of the appended claims.

In addition, well known power/ground connections to integrated circuit (IC) chips and other components may or may not be shown within the presented figures, for simplicity of illustration and discussion, and so as not to obscure the disclosure. Further, arrangements may be shown in block diagram form in order to avoid obscuring the disclosure, and also in view of the fact that specifics with respect to implementation of such block diagram arrangements are highly dependent upon the platform within which the present disclosure is to be implemented (i.e., such specifics should be well within purview of one skilled in the art). Where specific details (e.g., circuits) are set forth in order to describe example embodiments of the disclosure, it should be apparent to one skilled in the art that the disclosure can be practiced without, or with variation of, these specific details. The description is thus to be regarded as illustrative instead of limiting.

The following examples pertain to further embodiments. Specifics in the examples may be used anywhere in one or more embodiments. All optional features of the apparatus described herein may also be implemented with respect to a method or process.

For example, an apparatus is provided which comprises: a current source to generate a current having AC and DC components; a current-to-voltage converter to convert the current or a copy of the current to a voltage proportional to a resistance, the voltage having AC and DC components that correspond to the AC and DC components of the current; a first sample-and-hold circuit to sample and filter the AC component from the voltage and to provide an output voltage with the DC component; a second sample-and-hold circuit to sample the output voltage; a voltage-to-current converter to convert the sampled output voltage to a corresponding current; and an amplifier to receive the output voltage.

In some embodiments, the amplifier has: a non-inverting input, and wherein the output voltage is to be received by the non-inverting input; and an inverting input which is to act to sum to zero currents at the inverting input. In some embodiments, the amplifier has an output coupled to the inverting input via a first resistor having a resistance which is substantially equal to a resistance of a second resistor of the current-to-voltage converter. In some embodiments, a terminal of the first resistor is coupled to an output of the voltage-to-current converter. In some embodiments, the output voltage is to function as a reference voltage, and wherein the current-to-voltage converter is to cause the output voltage to lower in voltage level as the DC component of the current increases.

In some embodiments, the first sample-and-hold circuit is operable to sample the voltage at a first phase of a switching signal, and the second sample-and-hold circuit is to sample the output voltage at a second phase of the switching signal. In some embodiments, the first phase has a duration proportional to a duration the current source generates the current, and wherein the second phase has a duration which is proportional to a duration the current source does not generate the current. In some embodiments, the apparatus comprises a light source to input light to a media, wherein the current source is to detect the input light scattered from the media. In some embodiments, the current source is a photodiode, and wherein the light source is a Light Emitting Diode (LED). In some embodiments, the voltage-to-current converter has a configurable current gain.

In another example, a wearable device is provided which comprises: a light source to provide light to a media; a current source to detect a version of the light from the media and, from the version of the light, wherein the current source is to generate a first current having AC and DC components; an offset cancellation apparatus to receive the first current, the offset cancellation apparatus including: a first feedback electrical path including: a current-to-voltage converter coupled to the current source, a first sample and hold circuit coupled to the current-to-voltage converter, a filter coupled to the first sample and hold circuit, an amplifier coupled the filter, and a first resistor coupled to the amplifier and the current source; and a second feedback electrical path including: a second sample and hold circuit coupled to the filter and the amplifier of the first feedback electrical path, and a voltage-to-current converter coupled to the second sample and hold circuit and the current source; and a processing intellectual property (IP) block to receive a filtered version of an output of the amplifier and to determine a condition of the media according to the output voltage.

In some embodiments, the wearable device comprises a wireless interface for allowing the processing IP block to communicate with another device. In some embodiments, the wearable device comprises: a level shifter to level shift the output voltage to a lower voltage level; and a track-and-hold circuit to track the level-shifted output voltage and then to hold it. In some embodiments, the wearable device comprises a gain stage with a low pass filter, wherein the gain stage is to amplify the output of the track-and-hold circuit and is to filter the amplified output.

In some embodiments, the wearable device comprises an analog-to-digital converter to convert the filtered amplified output to a digital representation which is the filtered version of the output voltage provided to the processing IP block. In some embodiments, the wearable device comprises a light source driver, wherein the processing IP block is operable to adjust intensity of the light emitted by the light source by controlling the light source driver. In some embodiments, the media is part of a living body, and wherein the condition is a heartbeat.

In another example, an apparatus is provided which comprises: a first feedback electrical path including: a current-to-voltage converter coupled to a current source, a first sample and hold circuit coupled to the current-to-voltage converter, a filter coupled to the first sample and hold circuit, an amplifier coupled the filter, and a first resistor coupled to the amplifier and the current source; and a second feedback electrical path including: a second sample and hold circuit coupled to the filter and the amplifier of the first feedback electrical path, and a voltage-to-current converter coupled to the second sample and hold circuit and the current source.

In some embodiments, the first feedback electrical path is operable to make continuous time changes during a first phase of a signal to an output of the amplifier according to a scaled voltage representation of a DC component of a first current generated by the current source, and wherein the output of the amplifier is a second current to be added to the first current. In some embodiments, the second feedback electrical path is operable to generate a third current according to an input of the amplifier by sampling an output of the first sample and hold circuit during a second phase, wherein the third current is to be added to the first current during the first phase. In some embodiments, the current source is a photodiode.

In another example, a method is provided which comprises: generating a current having AC and DC components; converting the current or a copy of the current to a voltage proportional to a resistance, the voltage having AC and DC components that correspond to the AC and DC components of the current; sampling and filtering the AC component from the voltage and to provide an output voltage with the DC component; sampling the output voltage; converting the sampled output voltage to a corresponding current; and receiving the output voltage by amplifier.

In some embodiments, receiving the output voltage comprises: receiving the output voltage by a non-inverting input of the amplifier, and wherein the amplifier comprises an inverting input which is to act to sum to zero currents at the inverting input. In some embodiments, the amplifier has an output coupled to the inverting input via a first resistor having a resistance which is substantially equal to a resistance of a second resistor of the current-to-voltage converter. In some embodiments, a terminal of the first resistor is coupled to an output of the voltage-to-current converter. In some embodiments, the output voltage is to function as a reference voltage, and wherein the current-to-voltage converter is to cause the output voltage to lower in voltage level as the DC component of the current increases.

In another example, an apparatus is provided which comprises: means for generating a current having AC and DC components; means for converting the current or a copy of the current to a voltage proportional to a resistance, the voltage having AC and DC components that correspond to the AC and DC components of the current; means for sampling and filtering the AC component from the voltage and to provide an output voltage with the DC component; means for sampling the output voltage; means for converting the sampled output voltage to a corresponding current; and means for receiving the output voltage by amplifier.

In some embodiments, the means for receiving the output voltage comprises: means for receiving the output voltage by a non-inverting input of the amplifier, and wherein the amplifier comprises an inverting input which is to act to sum to zero currents at the inverting input.

An abstract is provided that will allow the reader to ascertain the nature and gist of the technical disclosure. The abstract is submitted with the understanding that it will not be used to limit the scope or meaning of the claims. The following claims are hereby incorporated into the detailed description, with each claim standing on its own as a separate embodiment.

What is claimed is:
1. An apparatus comprising:
a current source to generate a current having AC and DC components;
a current-to-voltage converter to convert the current or a copy of the current to a voltage proportional to a resistance, the voltage having AC and DC components that correspond to the AC and DC components of the current;
a first sample-and-hold circuit to sample and filter the AC component from the voltage and to provide an output voltage with the DC component;

a second sample-and-hold circuit to sample the output voltage;
a voltage-to-current converter to convert the sampled output voltage to a corresponding current; and
an amplifier to receive the output voltage.

2. The apparatus of claim 1, wherein the amplifier has:
a non-inverting input, and wherein the output voltage is to be received by the non-inverting input; and
an inverting input which is to act to sum to zero currents at the inverting input.

3. The apparatus of claim 2, wherein the amplifier has an output coupled to the inverting input via a first resistor having a resistance which is substantially equal to a resistance of a second resistor of the current-to-voltage converter.

4. The apparatus of claim 3, wherein a terminal of the first resistor is coupled to an output of the voltage-to-current converter.

5. The apparatus of claim 3, wherein the output voltage is to function as a reference voltage, and wherein the current-to-voltage converter is to cause the output voltage to lower in voltage level as the DC component of the current increases.

6. The apparatus of claim 1, wherein:
the first sample-and-hold circuit is operable to sample the voltage at a first phase of a switching signal, and
the second sample-and-hold circuit is to sample the output voltage at a second phase of the switching signal.

7. The apparatus of claim 6, wherein the first phase has a duration proportional to a duration the current source generates the current, and wherein the second phase has a duration which is proportional to a duration the current source does not generate the current.

8. The apparatus of claim 1 comprises a light source to input light to a media, wherein the current source is to detect the input light scattered from the media.

9. The apparatus of claim 8, wherein the current source is a photodiode, and wherein the light source is a Light Emitting Diode (LED).

10. The apparatus of claim 1, wherein the voltage-to-current converter has a configurable current gain.

* * * * *